United States Patent
Scarrott et al.

(10) Patent No.: US 12,415,048 B2
(45) Date of Patent: Sep. 16, 2025

(54) INTEGRATED DOSE COUNTER

(71) Applicant: Trudell Medical International, London (CA)

(72) Inventors: Peter Scarrott, London (CA); Michal Fulmyk, London (CA); Dawid Halupka, Toronto (CA); Justin Kim, Thornhill (CA); David Lynch, Burlington (CA)

(73) Assignee: TRUDELL MEDICAL INTERNATIONAL INC., London (CA)

( * ) Notice: Subject to any disclaimer, the term of this patent is extended or adjusted under 35 U.S.C. 154(b) by 793 days.

(21) Appl. No.: 17/118,177

(22) Filed: Dec. 10, 2020

(65) Prior Publication Data

US 2021/0170120 A1 Jun. 10, 2021

Related U.S. Application Data

(60) Provisional application No. 62/956,846, filed on Jan. 3, 2020, provisional application No. 62/946,259, filed on Dec. 10, 2019.

(51) Int. Cl.
*A61M 15/00* (2006.01)

(52) U.S. Cl.
CPC ...... *A61M 15/0083* (2014.02); *A61M 15/009* (2013.01); *A61M 2202/064* (2013.01); *A61M 2205/18* (2013.01); *A61M 2205/3313* (2013.01); *A61M 2205/3375* (2013.01); *A61M 2205/3553* (2013.01); *A61M 2205/3584* (2013.01); *A61M 2205/3592* (2013.01); *A61M 2205/502* (2013.01); *A61M 2205/52* (2013.01); *A61M 2205/581* (2013.01); *A61M 2205/583* (2013.01)

(58) Field of Classification Search
CPC .......... A61M 15/0068; A61M 15/0073; A61M 15/0075; A61M 15/0065
See application file for complete search history.

(56) References Cited

U.S. PATENT DOCUMENTS

| 4,460,412 A | 7/1984 | Imura et al. |
|---|---|---|
| 5,012,803 A | 5/1991 | Foley et al. |
| 5,167,506 A | 12/1992 | Kilis et al. |

(Continued)

FOREIGN PATENT DOCUMENTS

| EP | 0 746 366 B1 | 1/2002 |
|---|---|---|
| EP | 1 837 638 A1 | 9/2007 |

(Continued)

OTHER PUBLICATIONS

International Search Report and Written Opinion for International Application No. PCT/IB2022/059308 mailed Dec. 23, 2022 (15 pages).

(Continued)

*Primary Examiner* — Courtney B Fredrickson
(74) *Attorney, Agent, or Firm* — Crowell & Moring LLP

(57) ABSTRACT

An indicating device includes a mechanical dose counter adapted to count the number of doses that have been dispensed from or remain in a container and an electronic module coupled to the mechanical dose counter and adapted to record when the doses have been dispensed from the container. Methods of using and assembling the device are also provided.

19 Claims, 29 Drawing Sheets

(56) References Cited

U.S. PATENT DOCUMENTS

| | | |
|---|---|---|
| 5,368,842 A | 11/1994 | Lederman et al. |
| 5,404,871 A | 4/1995 | Goodman et al. |
| 5,505,192 A | 4/1996 | Samiotes et al. |
| 5,542,410 A | 8/1996 | Goodman et al. |
| 5,544,647 A | 8/1996 | Jewett et al. |
| 5,622,163 A | 4/1997 | Jewett et al. |
| 5,676,129 A | 10/1997 | Rocci, Jr. et al. |
| 6,029,659 A | 2/2000 | O'Connor |
| 6,033,392 A * | 3/2000 | Frey .................. B65D 81/24 |
| | | 206/365 |
| 6,076,521 A | 6/2000 | Lindahl et al. |
| 6,082,358 A | 7/2000 | Scarrott et al. |
| 6,190,326 B1 | 2/2001 | McKinnon et al. |
| 6,202,642 B1 | 3/2001 | McKinnon et al. |
| 6,926,002 B2 | 8/2005 | Scarrott et al. |
| 6,958,691 B1 | 10/2005 | Anderson et al. |
| 7,047,964 B2 | 5/2006 | Bacon |
| 7,347,200 B2 | 3/2008 | Jones et al. |
| 7,597,099 B2 | 10/2009 | Jones et al. |
| 7,726,303 B2 | 6/2010 | Tyvoll et al. |
| 7,779,835 B2 | 8/2010 | Hamano |
| 7,926,484 B2 | 4/2011 | Dhuper et al. |
| 8,056,556 B2 | 11/2011 | Childers et al. |
| 8,074,594 B2 | 12/2011 | Lu |
| 8,240,303 B2 | 8/2012 | Hamano |
| 8,342,172 B2 | 1/2013 | Levy et al. |
| 8,424,517 B2 | 4/2013 | Sutherland et al. |
| 8,539,945 B2 | 9/2013 | Solomon et al. |
| 8,695,587 B2 | 4/2014 | Imran |
| 8,807,131 B1 | 8/2014 | Tunnell et al. |
| 8,814,035 B2 | 8/2014 | Stuart |
| 9,004,062 B2 | 4/2015 | Lang et al. |
| 9,035,765 B2 | 5/2015 | Engelhard et al. |
| 9,072,846 B2 | 7/2015 | Helmlinger |
| 9,242,056 B2 | 1/2016 | Andersen et al. |
| 9,247,534 B2 | 1/2016 | Han et al. |
| 9,272,102 B1 | 3/2016 | Yu et al. |
| 9,381,313 B2 | 7/2016 | Bari |
| 9,427,534 B2 | 8/2016 | Bruin et al. |
| 9,427,934 B2 | 8/2016 | Tsuchiya et al. |
| 9,463,291 B2 | 10/2016 | Imran |
| 9,468,729 B2 | 10/2016 | Sutherland et al. |
| 9,517,314 B2 | 12/2016 | Hately et al. |
| 9,550,031 B2 | 1/2017 | Van Sickle et al. |
| 9,626,481 B2 | 4/2017 | Solomon et al. |
| 9,728,068 B2 | 8/2017 | Engelhard et al. |
| 9,782,550 B2 | 10/2017 | Morrison et al. |
| 9,782,551 B2 | 10/2017 | Morrison et al. |
| 9,943,656 B2 | 4/2018 | Shears et al. |
| 10,002,517 B2 | 6/2018 | Engelhard et al. |
| 10,155,094 B2 | 12/2018 | Wachtel et al. |
| 10,173,020 B2 | 1/2019 | Sutherland et al. |
| 10,220,166 B2 | 3/2019 | Van Sickle et al. |
| 10,300,227 B2 | 5/2019 | Sutherland et al. |
| 10,406,304 B2 | 9/2019 | Koerner |
| 10,463,816 B2 | 11/2019 | Calderon Oliveras et al. |
| 10,556,070 B2 | 2/2020 | Van Sickle et al. |
| 10,569,034 B2 | 2/2020 | Morrison et al. |
| 10,573,161 B2 | 2/2020 | Engelhard et al. |
| 10,668,232 B2 | 6/2020 | Sutherland et al. |
| 10,688,261 B2 | 6/2020 | Van Sickle et al. |
| 10,729,861 B2 | 8/2020 | Turner et al. |
| 10,729,863 B2 | 8/2020 | Meyer et al. |
| 2003/0183226 A1 | 10/2003 | Brand et al. |
| 2004/0231667 A1 | 11/2004 | Horton et al. |
| 2004/0255936 A1 | 12/2004 | Urbanus |
| 2005/0028815 A1 | 2/2005 | Deaton et al. |
| 2005/0076904 A1 * | 4/2005 | Jones .................. A61M 15/009 |
| | | 128/200.23 |
| 2005/0087191 A1 * | 4/2005 | Morton .................. A61M 15/009 |
| | | 128/200.23 |
| 2005/0172958 A1 | 8/2005 | Singer et al. |
| 2006/0130838 A1 | 6/2006 | Lee et al. |
| 2006/0254581 A1 | 11/2006 | Genova et al. |
| 2007/0084462 A1 | 4/2007 | Allen et al. |
| 2007/0091273 A1 | 4/2007 | Sullivan |
| 2007/0295329 A1 | 12/2007 | Lieberman et al. |
| 2008/0017193 A1 | 1/2008 | Jones et al. |
| 2008/0178872 A1 | 7/2008 | Genova et al. |
| 2008/0283062 A1 | 11/2008 | Esposito, Jr. |
| 2009/0050142 A1 | 2/2009 | Hamano |
| 2009/0151718 A1 | 6/2009 | Hunter et al. |
| 2009/0194104 A1 | 8/2009 | Van Sickle |
| 2009/0229607 A1 | 9/2009 | Brunnberg et al. |
| 2010/0192948 A1 | 8/2010 | Sutherland et al. |
| 2011/0031038 A1 | 2/2011 | Page |
| 2011/0041845 A1 | 2/2011 | Solomon et al. |
| 2011/0253139 A1 | 10/2011 | Guthrie et al. |
| 2012/0055472 A1 | 3/2012 | Brunnberg et al. |
| 2012/0247467 A1 | 10/2012 | Borm et al. |
| 2013/0092158 A1 | 4/2013 | Levy et al. |
| 2013/0151162 A1 | 6/2013 | Harris et al. |
| 2013/0172690 A1 | 7/2013 | Arne et al. |
| 2014/0182584 A1 | 7/2014 | Sutherland et al. |
| 2014/0216444 A1 | 8/2014 | Shtram et al. |
| 2014/0243709 A1 | 8/2014 | Gibson et al. |
| 2015/0100276 A1 | 4/2015 | Huang et al. |
| 2015/0100335 A1 | 4/2015 | Engelhard et al. |
| 2015/0174348 A1 * | 6/2015 | Tunnell .................. A61M 16/021 |
| | | 128/200.14 |
| 2015/0290396 A1 | 10/2015 | Nagar et al. |
| 2016/0082208 A1 | 3/2016 | Ballam et al. |
| 2016/0144141 A1 | 5/2016 | Biswas et al. |
| 2016/0166766 A1 | 6/2016 | Schuster et al. |
| 2017/0127945 A1 | 5/2017 | Reed |
| 2018/0085540 A1 | 3/2018 | Dantsker et al. |
| 2018/0093053 A1 | 4/2018 | Turner et al. |
| 2018/0126099 A1 | 5/2018 | Verjus et al. |
| 2018/0140796 A1 | 5/2018 | Haibach et al. |
| 2018/0184923 A1 | 7/2018 | Tal et al. |
| 2018/0221600 A1 | 8/2018 | Shears et al. |
| 2018/0236107 A1 | 8/2018 | Kwok et al. |
| 2018/0308572 A1 | 10/2018 | Manice et al. |
| 2019/0030263 A1 | 1/2019 | Calderon Oliveras et al. |
| 2019/0030267 A1 | 1/2019 | Morrison et al. |
| 2019/0105450 A1 | 4/2019 | Sutherland et al. |
| 2019/0125990 A1 | 5/2019 | Holtz et al. |
| 2019/0134321 A1 | 5/2019 | Calderon Oliveras et al. |
| 2019/0151577 A1 | 5/2019 | Jung et al. |
| 2019/0192779 A1 | 6/2019 | Nagar et al. |
| 2019/0224426 A1 | 7/2019 | Farina et al. |
| 2019/0231993 A1 | 8/2019 | Van Sickle et al. |
| 2019/0275267 A1 | 9/2019 | Calderon Oliveras et al. |
| 2019/0385727 A1 * | 12/2019 | Manice .................. G16H 40/63 |
| 2020/0001026 A1 | 1/2020 | Starr et al. |
| 2020/0155773 A1 | 5/2020 | Zipkes et al. |
| 2020/0155775 A1 | 5/2020 | Keppner et al. |
| 2020/0188013 A1 | 6/2020 | Batchelor et al. |
| 2020/0188613 A1 | 6/2020 | Van Sickle et al. |
| 2020/0254197 A1 | 8/2020 | Van Sickle et al. |
| 2020/0268990 A1 | 8/2020 | Ash |
| 2021/0170120 A1 | 6/2021 | Scarrott et al. |

FOREIGN PATENT DOCUMENTS

| | | |
|---|---|---|
| EP | 3 431 127 A1 | 1/2019 |
| EP | 2 911 717 B1 | 5/2019 |
| EP | 3 739 591 A1 | 11/2020 |
| GB | 2 262 452 A | 6/1993 |
| GB | 2 552 539 A | 1/2018 |
| WO | WO 96/16686 A1 | 6/1996 |
| WO | WO 2005/084738 A1 | 9/2005 |
| WO | WO 2007/031740 A1 | 3/2007 |
| WO | WO 2007/088367 A1 | 8/2007 |
| WO | WO 2008/006527 A1 | 1/2008 |
| WO | WO 2009/022139 A1 | 2/2009 |
| WO | WO 2009/141171 A2 | 11/2009 |
| WO | WO 2014/068504 A2 | 5/2014 |
| WO | WO 2014/123858 A1 | 8/2014 |
| WO | WO 2015/172897 A1 | 11/2015 |
| WO | WO 2017/174588 A1 | 10/2017 |
| WO | WO 2017/178865 A1 | 10/2017 |

(56) References Cited

FOREIGN PATENT DOCUMENTS

WO     WO 2018/063795 A1     4/2018
WO     WO 2019/022620 A1     1/2019

OTHER PUBLICATIONS

International Search Report and Written Opinion of the International Application No. PCT/IB2020/061748, dated Mar. 17, 2021, 11 pp.

* cited by examiner

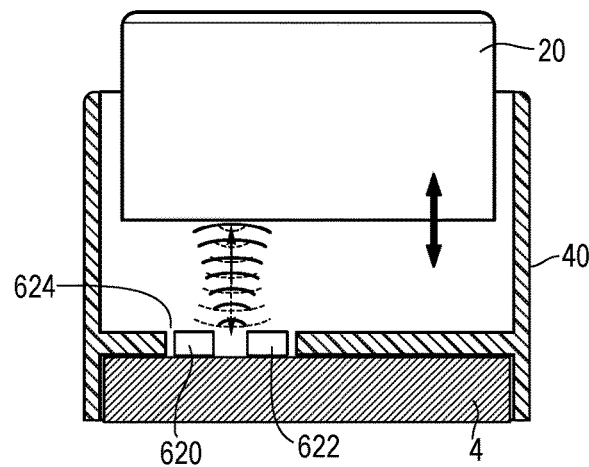
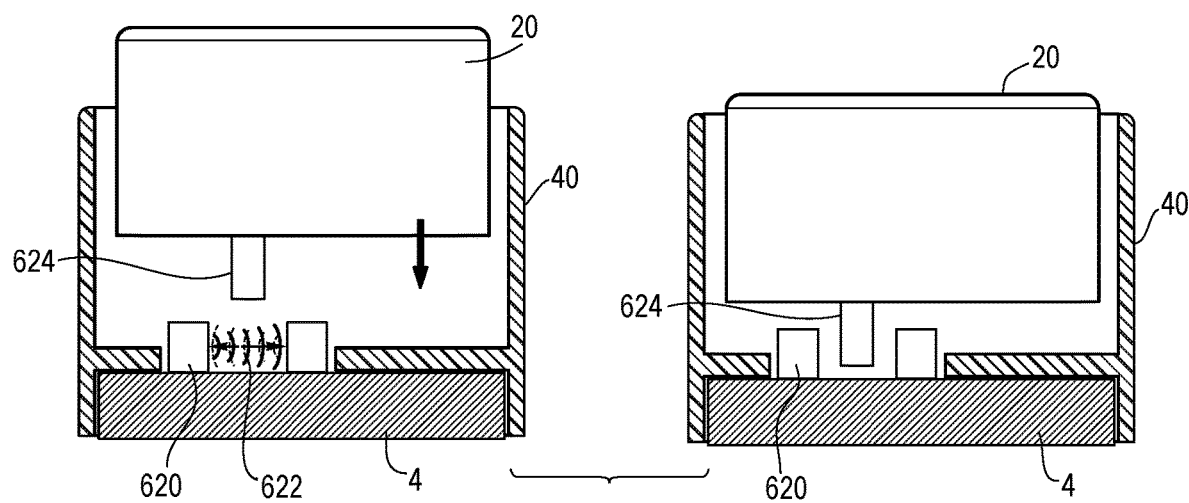

NOTES:
ACC - accelerometer
$f_{s,ACC}$ - accelerometer sampling rate
INT - interrupt signal
$t_{TX}$ - BLE timeout period
IR detection <-

VARIABLES
In:
- Dose counter
- Time stamp

Out:
- N/A

Internal:
- N/A

INTEGRATED DOSE COUNTER

This application claims the benefit of U.S. Provisional Application No. 62/946,259, filed Dec. 10, 2019 and entitled "Integrated Dose Counter," and claims the benefit of U.S. Provisional Application No. 62/956,846, filed Jan. 3, 2020 and entitled "Integrated Dose Counter," the entire disclosures of which are hereby incorporated herein by reference.

TECHNICAL FIELD

The present invention relates generally to a dose counter, and in particular to an integrated dose counter including a mechanical dose counter and an electronic module, and also to methods of delivering aerosol medicament or the like and methods of assembling the integrated dose counter.

BACKGROUND

Metered dose inhalers (MDI's) are not reusable devices and so are disposed of after their prefilled number of doses have been administered or have exceeded the specified shelf life of the drug. Mechanical dose counting mechanisms may be integrated with MDI's, and may be required by the FDA. There are two common types of mechanical dose counters that use either (1) displacement of the MDI canister relative to the actuator or (2) force applied to the MDI as the means of detecting and therefore counting an actuation or release of a dose. Mechanical dose counters typically are only able to provide information about the number of doses dispensed from or remaining in the container, and typically do not provide information about how the dose was taken or when.

BRIEF SUMMARY

In one aspect, one embodiment of an indicating device includes a mechanical dose counter adapted to count the number of doses that have been dispensed from or remain in a container and an electronic module coupled to the mechanical dose counter and adapted to record when the doses have been dispensed from the container.

In another aspect, one embodiment of a method of assembling a medicament dispensing device includes coupling a mechanical dose counter adapted to count the number of doses that have been dispensed from or remain in a container to an electronic module adapted to record when the doses have been dispensed from the container, coupling at least one of the mechanical dose counter or the electronic module to the container or an actuator housing, and coupling the container to the actuator housing.

In another aspect, a method of counting a dose dispensed from a medicament dispensing device includes pushing one of a mechanical dose counter or an electronic module coupled to the mechanical dose counter, wherein at least one of the mechanical dose counter and electronic module are coupled to a container or an actuator housing holding the container, dispensing a dose of medicament from the container, counting the dose of medicament dispensed from the container with the mechanical dose counter and displaying the number of doses that have been dispensed from or remain in the container with the mechanical dose counter, and recording when the dose of medicament was dispensed from the container with the electronic module.

BRIEF DESCRIPTION OF THE DRAWINGS

FIG. 11 is a cross-sectional view of one embodiment of a mechanical dose counter coupled to an electronic module.

FIG. 12 is a cross-sectional view of one embodiment of a mechanical dose counter coupled to an electronic module.

DETAILED DESCRIPTION OF THE DRAWINGS AND THE PRESENTLY PREFERRED EMBODIMENTS

Overall Embodiment Description

Figure 1:
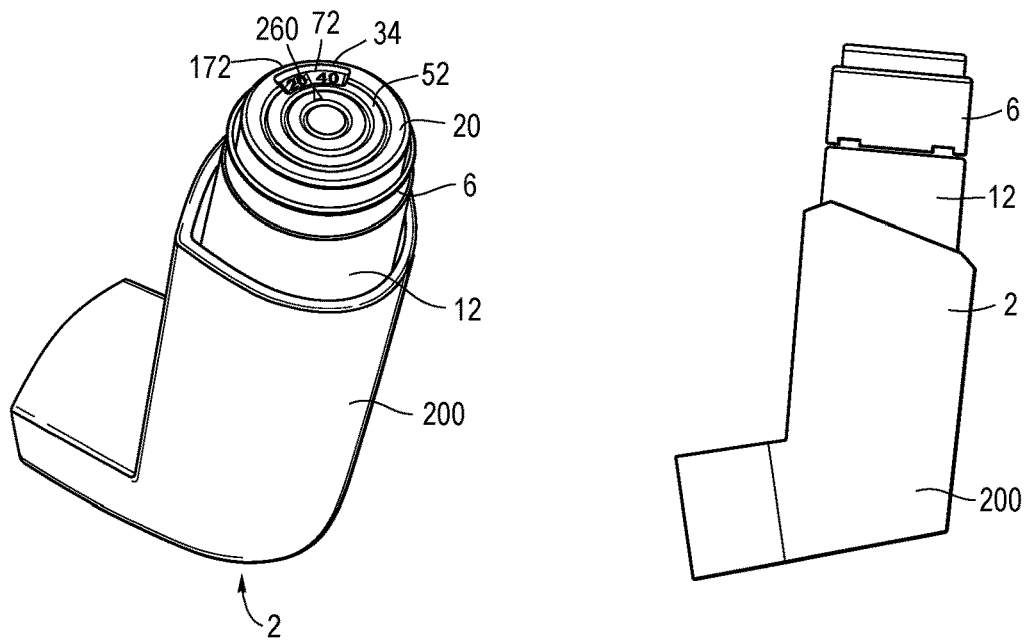
FIG. 1 is a perspective and side view of a metered dose inhaler with a mechanical dose counter coupled to a container.
Figure 2:
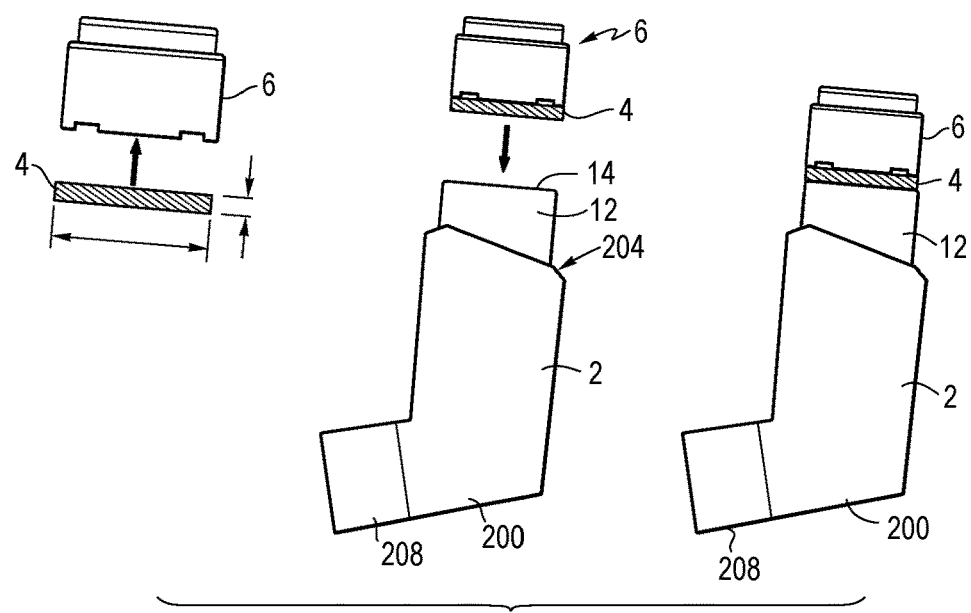
FIG. 2 are side views of a mechanical dose counter and electronic module applied to a metered dose inhaler.
Figure 4:
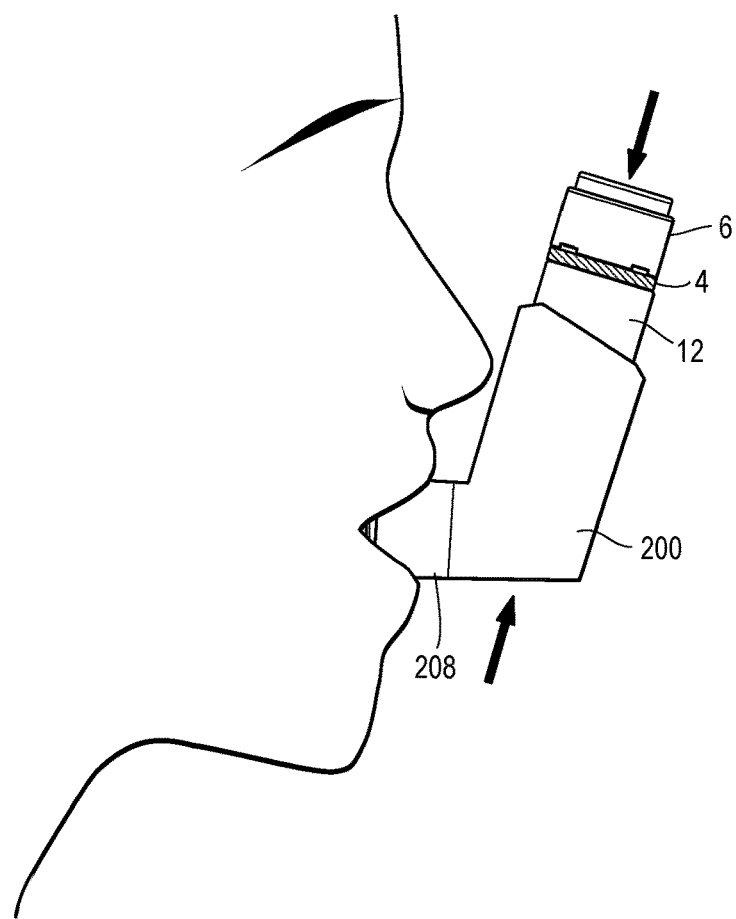
FIG. 4 is a side view of a metered dose inhaler with a mechanical dose counter and electronic module being actuated.

In one aspect, one embodiment of an indicating device provides mechanical dose counting and electronic dose counting, which would also enable additional information to be captured and communicated externally of a medication delivery device or system, including for example and without limitation a metered dose inhaler (MDI) 2, shown for example in FIGS. 1, 2 and 4. For example, such information may assist in determining whether a patient was adherent to their prescribed treatment where adherence can be described as persistence, whether the medication was taken and was taken at the right time, and whether there was compliance, i.e., was the medication taken properly.

The electronic dose counting and tracking module (EM) 4 is very low cost and may be easily integrated with existing MDI's that are already manufactured on a very low cost platform. Secondly, the electronics are developed with a very small form factor, which is an advantage in that would be easier to integrate into existing MDI's, provide greater flexibility in how they are integrated, and have the least impact on overall MDI functionality and usability. Together with low cost and size requirements, the selection of electronics and components have very low energy consumption requirements while accurately and reliably detecting, storing, and communicating each actuation of the dose counter.

In one embodiment, the EM 4 is permanently attached to an existing mechanical dose counter, for example a mechanical top mounted actuation indicator (TMAI) 6, forming the electronic TMAI (eTMAI) assembly. The resulting eTMAI may then be non-removeably coupled to the canister portion of a pressurized metered dose inhaler (pMDI), for example by the pMDI manufacturer using an adhesive label wrap 600, 1600, 1602. The EM 4 provides additional connectivity, enhanced functionality, and adherence tracking to the existing TMAI 6, while maintaining the mechanical dose counting functionality.

Preferred Embodiment—Electro-mechanical Dose Counter and Tracker Description

One mechanical dose counter is a TMAI 6, for example as manufactured by Trudell Medical International, which is a force type dose counter. Various examples of the dose counter are disclosed in U.S. Pat. Nos. 6,082,358, 6,926,002 and 8,074,594, the entire disclosures or which are hereby incorporated herein by reference. (No license, expressed or implied, is intended to be granted to either of these patents by reason of the incorporation by reference herein).

Referring to the drawings, and in particular FIGS. 1, 2, 4, 13-20, 34, 37, 40 and 42A and B, an aerosol dispenser is shown as including a housing 200, or actuator boot, and a container 12 disposed therein. The housing has a longitudinally extending cavity 202 shaped to receive the container. A top portion of the housing is generally open such that the container can be inserted in the housing through opening 204 and be installed therein with a bottom end 14 of the container protruding from the housing so as to be exposed to the user for actuation.

The terms "longitudinal" and "axial" as used herein are intended to indicate the direction of the reciprocal movement of the container relative to the housing, and of an indicating device cap member relative to a base member. The terms "top," "bottom," "upwardly" and "downwardly" are intended to indicate directions when viewing the inhalation devices as shown in the Figures, but with the understanding that the container is inverted such that the top surface thereof is located adjacent the bottom of the housing and vice versa. Moreover, it should be understood that a user can use the container and dispenser in any number of positions, including but not limited to the preferred upright position shown in FIGS. 1, 2, 4, 13 and 14.

Figure 13:
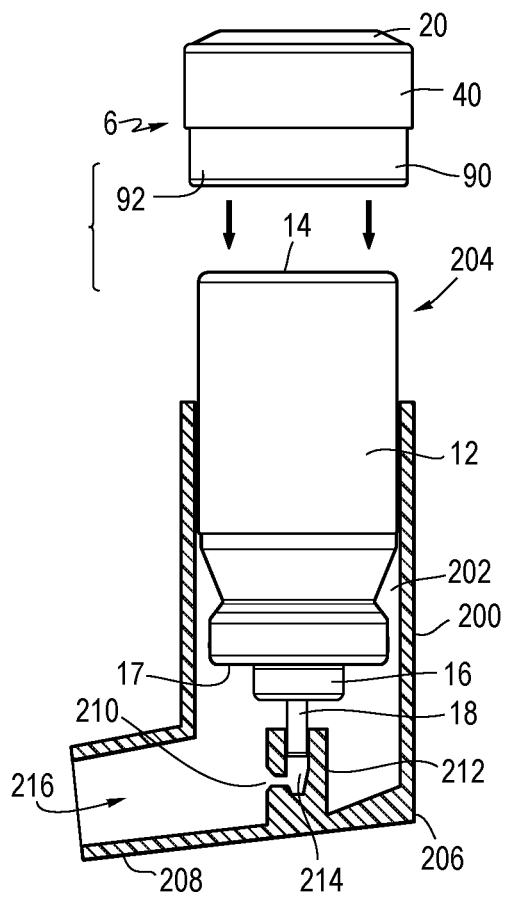
FIGS. 13 and 14 are a cross-sectional view of a metered dose inhaler with a mechanical dose indicator applied thereto.
Figure 14:
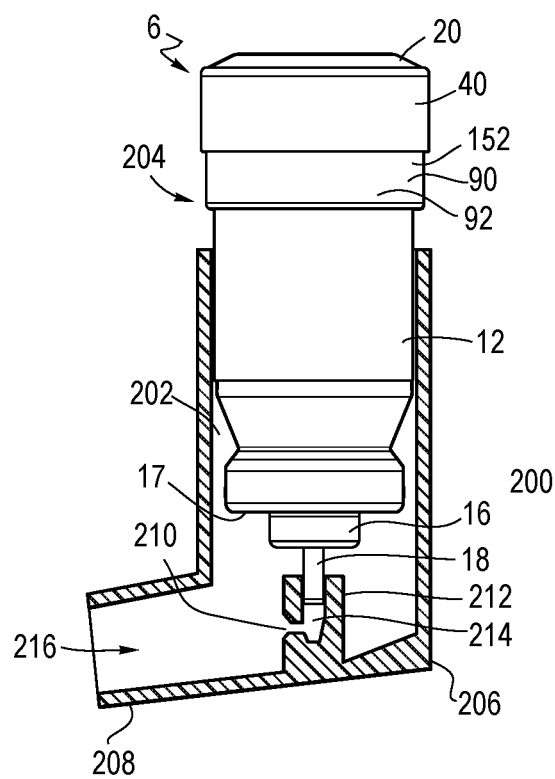

As shown in FIGS. 13 and 14, a cylindrical support block 212 having a well 214 is formed in a bottom portion 206 of the housing. An orifice 210 penetrates the support block to communicate with a bottom portion of the well. In one embodiment, a mouthpiece 208, intended for insertion into the mouth of a patient, forms an exhaust port 216 that communicates with the orifice and well. The mouthpiece 208 extends laterally from the housing so as to facilitate insertion of the mouthpiece into the mouth of the patient.

The container 12 is cylindrical and has a hub 16 disposed on a top surface 17 thereof. A valve stem 18 extends longitudinally from the hub. The valve stem extends coaxially from the container and is biased outwardly therefrom by a spring (not shown) mounted within the valve stem of the container. The container 12 is mounted in the housing by press fitting the valve stem 18 in the well 214 of the support block.

In a preferred embodiment, the container 12 is filled with a pressurized aerosol and medicament which is dispensed therefrom in specific metered doses by depressing or moving the valve stem 18 from an extended closed position to a depressed open position. A single metered dose is dispensed from the container by each reciprocal, longitudinal movement of the valve stem.

In operation, the opening of the valve stem is effected by moving the container 12 reciprocally within the housing 200 along a longitudinal axis, defined by the valve stem and the reciprocal movement of the container, by depressing the bottom end 14 of the container relative to the housing so as to move the valve stem 18 to the open position as it is supported within the well by the support block. As the valve stem is moved to the open position, the container dispenses a metered dose of aerosol and medicament through the well 214 and orifice 210. The aerosol and medicament are then transmitted to the patient through the exhaust port of the mouthpiece by way of either a self-generated or assisted airflow.

In other delivery systems, the housing and holder for the container are attached to a component having a chamber with an output end. Examples of these kinds of delivery systems are shown for example in U.S. Pat. No. 5,012,803, issued May 7, 1991, and U.S. Pat. No. 4,460,412, issued Sep. 11, 1984, both of which are hereby incorporated herein by reference. (No license, expressed or implied, is intended to be granted to either of these patents by reason of the incorporation by reference herein). In these kinds of delivery systems, the component having the chamber can be adapted to receive the mouthpiece of the housing, or it can be integrally connected with a holder supporting the container. In either embodiment, the metered dose of medicament in aerosol is first dispensed from the container into the chamber, and thereafter inhaled by the patient.

In a preferred embodiment, the container 12 is intended to dispense a predetermined number of metered doses of medicament. For example, conventional inhaler containers typically hold on the order of 100 to 200 metered doses. It should be understood, however, that the range of available doses could potentially vary from as few as one dose to as many as 500, or even more, depending, for example, on the capacity of the container, and/or the size of the metering dose valve. In operation, it can be important for the patient to be aware of the number of metered doses remaining in the container such that the patient is not caught unaware with an empty container when in need of the medicament.

Figure 29:
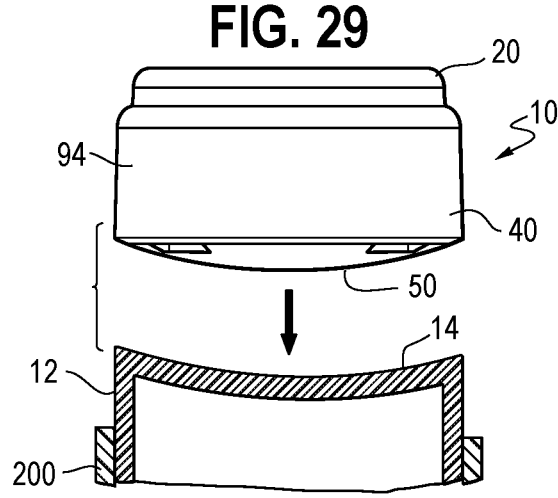
FIG. 29 is a cross-sectional view of a mechanical dose counter being applied to the bottom of a container.

Now generally referring to the Figures, a mechanical dose indicating device 6 is shown. The indicating device 6 indicates the number of metered doses that have been dispensed from or remain in the container. As shown in the embodiments of FIGS. 1, 2, 4, and 13-20, respectively, the indicating device 6 includes a cap member 20, 220, disposed in a base member 40. The base member 40 is configured such that it can be mounted to the bottom of the container 12. In a first embodiment, shown in FIGS. 15-18, 29 and 32, the base member includes a convex, or curved bottom portion 50, or floor, which is shaped to be received in and to mate with the bottom end 14 of the container, which has a concave or inwardly curved contour (see FIG. 29). The base member 40 is preferably bonded to the bottom of the container with adhesive, double sided tape, or similar bonding agent. Alternatively, a label 600, 1600, or other wrap component, may be wrapped around the base member and container, which have the same circumference in one embodiment. As shown in the embodiment of FIGS. 15-20 and 32, a circumferential skirt member 94 extends upwardly from the base portion to form a cavity 96.

Alternatively, as shown in FIGS. 13 and 14, the base member 90 includes a bottom portion, a downwardly depending circumferential skirt 152 and an upwardly depending circumferential skirt. Depending skirt 152 forms a recess or cavity which is shaped to receive the bottom end of the container 12. The base member is mounted on the container either by bonding one or more of the bottom portion or skirt to the container, or by press fitting the container in the cavity so as to provide an interference fit between the container and the depending skirt. The upwardly depending skirt and bottom portion form an upper cavity overlying the lower cavity.

Although the disclosed container and indicating device, and in particular, the cap member and base member, are shown as preferably having a circular cross section, those skilled in the art should understand that the container and indicating device, including any adapter, can be configured in other shapes, including for example, but not limited to, a rectangular or triangular cross-section.

As best shown in FIG. 1, the cap member 20 has a top portion 52 with a viewing window 34 formed therein. Preferably, the cap member 20 is circular and the viewing window is formed in the top portion adjacent the outer periphery of the cap member so as to overlie indicia applied to the top of an indicator member supported beneath the cap member. The viewing window can be configured in a number of various shapes. For example, the viewing window can be tapered, or it can be an arcuate shaped window bounded by coaxial inner and outer curved borders and radial side borders as shown in FIG. 1. The top of the cap member preferably has a plurality of raised portions or recesses forming a grippable pattern for the user's thumb, or finger. In this way, the user can firmly press down on the cap member without slippage. One of skill in the art should recognize that other patterns or grippable surfaces, such as a knurled pattern, can be applied to the cap member to facilitate the use of the indicating device.

Referring to FIGS. 13-20 and 32, the cap member 20, 220 comprises a circumferential skirt 92, 292 depending downwardly from the top portion 52, 252. The skirt preferably has a smaller diameter than the upwardly depending skirt of the base member, such that the cap member skirt nests within the upwardly extending skirt of the base member. Alternatively, the cap member can be configured with a skirt having a larger diameter than the skirt of the base member such that the base member skirt nests in the cap member skirt. The cap member 20, 220 is moveably mounted to the base member 40 by way of a snap fit.

Figure 19:
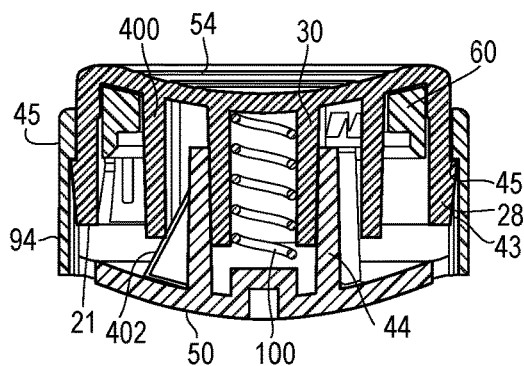
FIG. 19 is a cross-sectional view of one embodiment of a mechanical dose counter.

In particular, as shown in FIG. 19, the cap member includes a plurality of engagement members extending from an outer circumferential surface of the skirt that are captured in pockets formed along the inner circumferential surface of the base member skirt to form a snap-lock fit. In particular, the upper surface of the engagement member engages an engagement surface 45 defining the top of the pocket. In this way, the cap member is moveable with respect to the base member along an axial, or longitudinal, path. Alternatively, the rim of the base member can be curved slightly inward such that the engagement members engage the inwardly curved rim portion so as to prevent the cap member from being separated from the base member.

The axial movement of the cap member 20, 220 relative to the base member 40 is bounded or constrained by the engagement of the engagement members with the top of the base member pockets (or the base member rim) at a fully extended position and by engagement of a bottom rim 21, 221 of the cap member skirt with the upper surface of the bottom portion at the bottom of the stroke as shown in FIGS. 15-18. One of skill in the art should understand that the engagement members can alternatively be formed on the base member skirt so as to engage pockets or openings, or a rim (or like protrusion), formed on the cap member skirt.

As shown in FIGS. 15-19 and 32, a spring 100 is disposed between the cap member and the base member. The spring is preferably disposed in a downwardly extending hub portion 30, 230 of the cap member and an upwardly extending hub portion 44 of the base member, which are received one in the other. Alternatively, a spring is disposed between the cap member and base member and is of such a size that the coils are positioned adjacent the inner circumferential surface of the cap member skirt. The spring 100 functions as a return mechanism and biases the cap member 60, 260 upwardly in the base member such that the engagement members 28, 228 of the cap member engage the upper portion of the pockets of the base member. Although a compression spring is shown in the Figures, it should be understood that a belleville washer, cantilever, torsion, leaf and/or tension springs would also work to bias the cap member upwardly into engagement with the base member. The springs can be made of metal or plastic.

Figure 20:
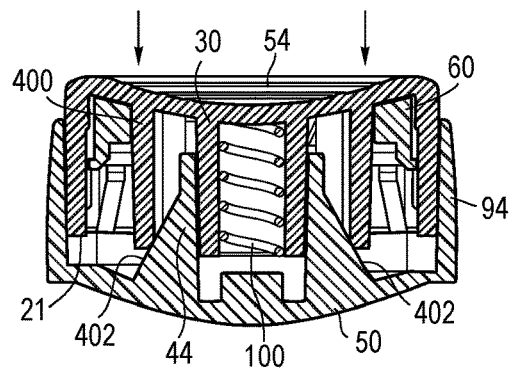
FIG. 20 is a cross-sectional view of one embodiment of a mechanical dose counter.
Figure 21:
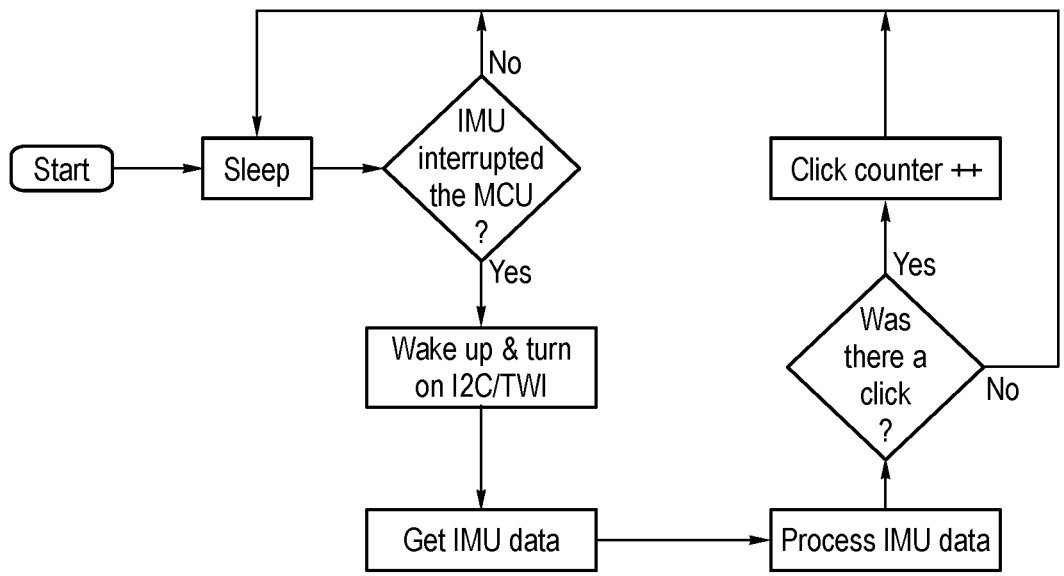
FIG. 21 is a flow chart showing the operation of one embodiment of an electronic module.
Figure 22:
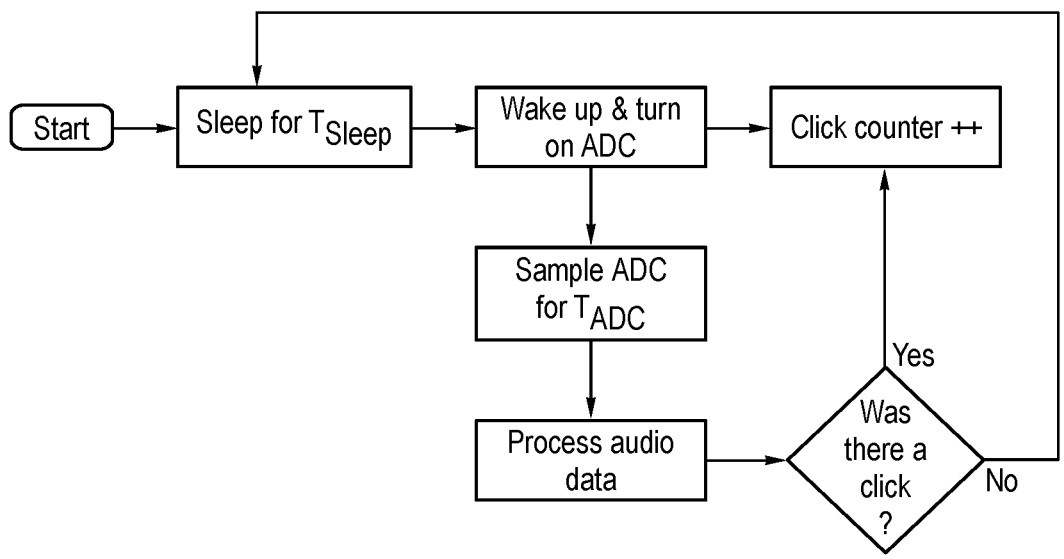
FIG. 22 is a flow chart showing the operation of one embodiment of an electronic module.
Figure 23:
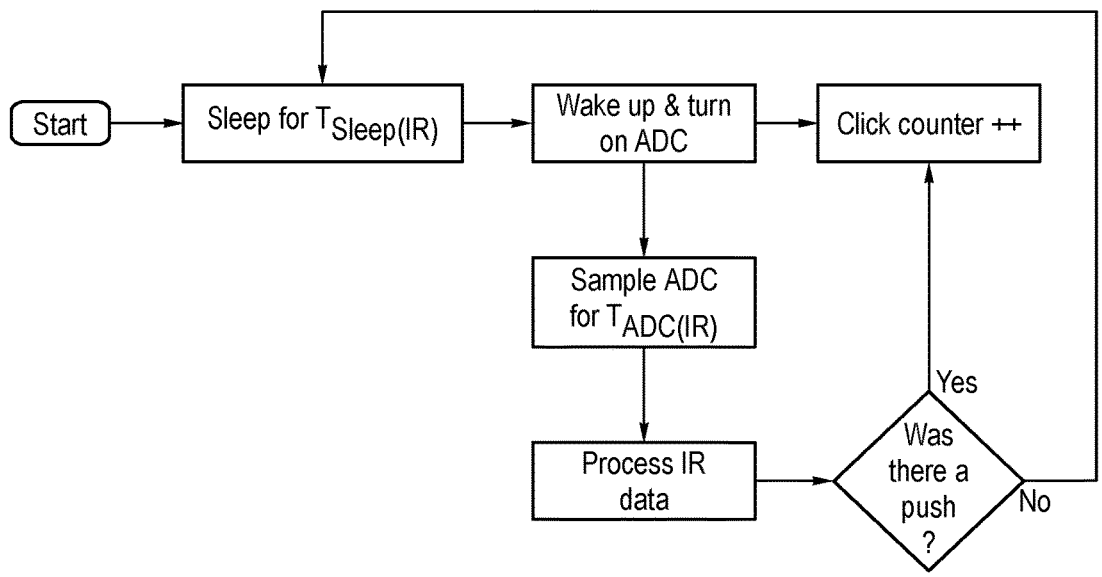
FIG. 23 is a flow chart showing the operation of one embodiment of an electronic module.
Figure 24:
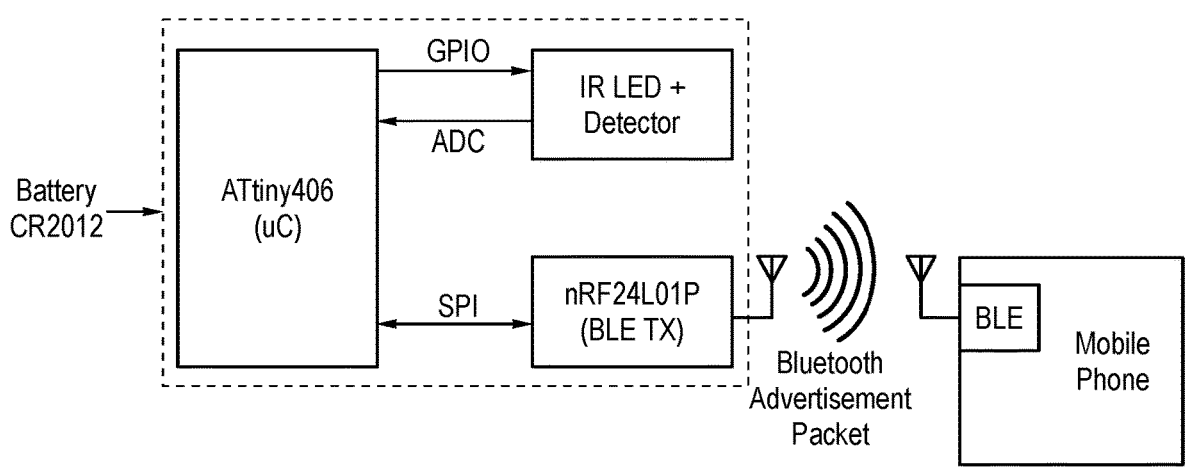
FIG. 24 is a schematic diagram of one embodiment of a system.
Figure 25:
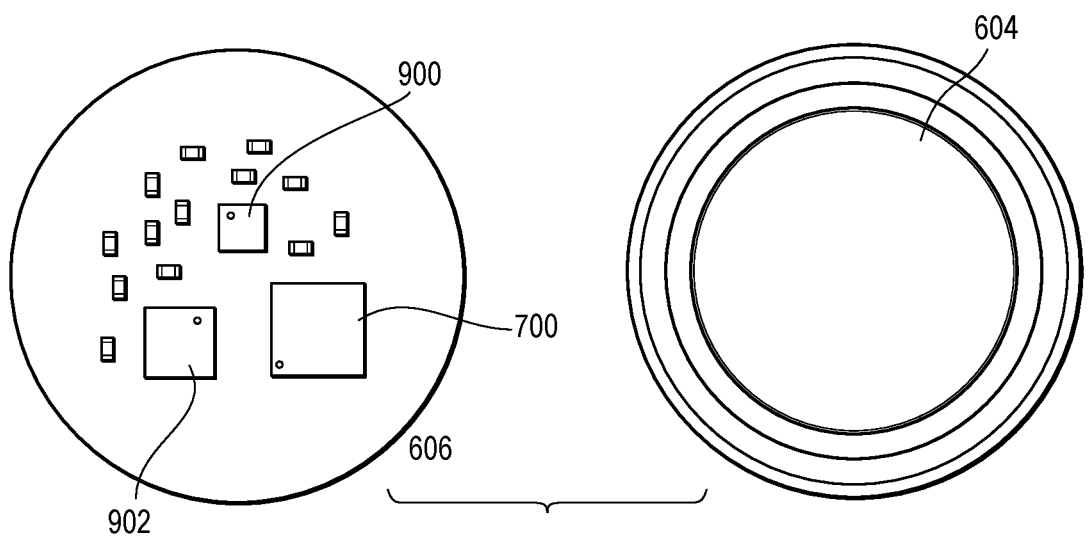
FIG. 25 are views of one embodiment of an electronic module.

As shown in FIG. 20, the return mechanism acting between the cap member and base member includes a plurality of resilient arm members 400 extending downwardly from the cap member. As the cap member is moved toward the base member, one or more of the arm members engages a ramped biasing surface 402 formed along an outer portion of the hub portion 44. The ramped biasing surface biases one or more of the resilient arm members outwardly as the cap member moves toward the base member. The resilient arm member(s) act as cantilever springs to bias the cap member away from the base member when the cap member is released by the user. One of skill in the art should understand that the resilient arm members can also be formed on the base member so as to engage a ramped surface formed on the cap member. One of skill in the art should also understand that the spring and resilient arm members can be used together, as shown in FIG. 20, or separately.

Referring to FIGS. 1, 15-20 and 32, an indicator member 260 is rotatably mounted in the cap member 20, 220 about an axis substantially parallel to the axial movement of the cap member relative to the base member. The indicator member is generally open in the middle and includes a top portion 276 having an upper surface 262 that rotatably slides along a bottom surface of the top portion of the cap member. Alternatively, the indicator member can be mounted on the outside of the cap member with a viewing window formed in the indicator member for viewing indicia applied to the top of the cap member.

Figure 5:
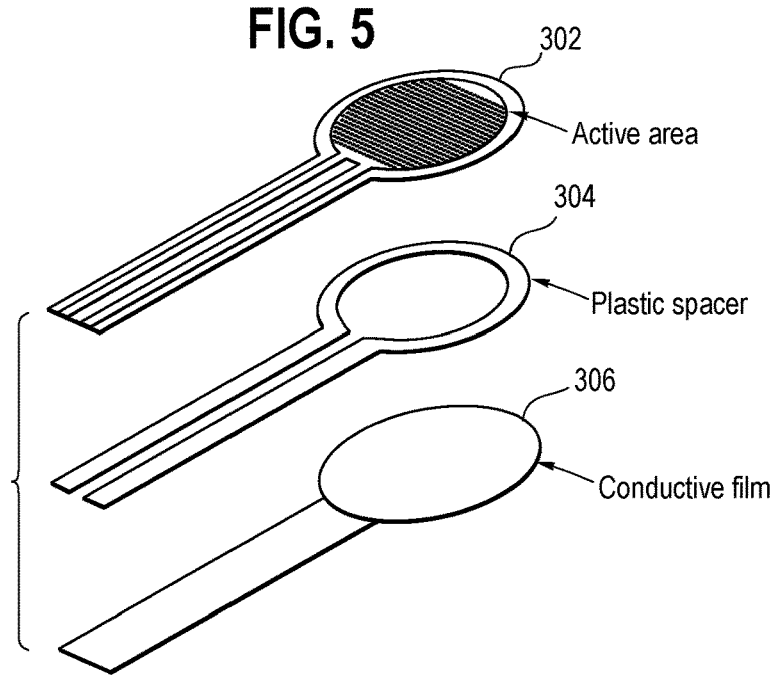
FIG. 5 is an exploded view of one embodiment of a force sensitive resistor assembly.
Figure 8:
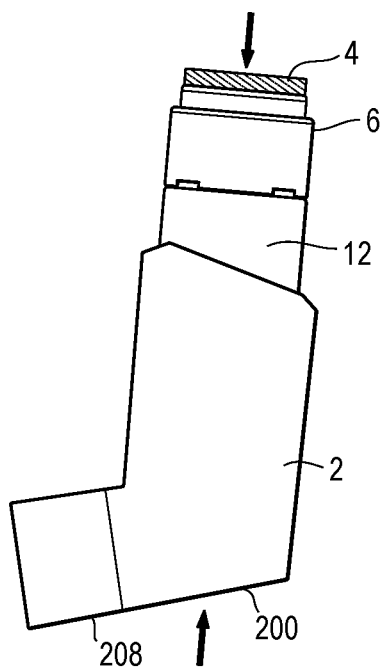
FIG. 8 is a side view of one embodiment of a mechanical dose counter and electronic module applied to a metered dose inhaler.

The indicator member 260 includes a circumferential skirt 274 depending downwardly from the top portion. Referring to FIGS. 5 and 8, a plurality of protrusions, or engagement tab members, extend from an inner circumferential surface of the cap member skirt and engage a rim 264 formed on the bottom of the indicator member skirt. Alternatively, the indicator member can include an engagement member, or rim, that engages a groove or similar opening in the cap member. In this way, the indicator member is secured to the cap member so as to prevent axial movement therebetween but where the indicator member is permitted to rotate relative to the cap member. The indicator member is installed by snap-fitting the indicator member within the cap member. One of skill in the art should understand that the indicator member could alternatively be rotatably mounted on the cap member hub portion (having a portion of the key member cut away), or on a similar axle secured to the cap member.

The indicator member 260 has a plurality of inwardly facing teeth 266 formed around the inner circumference of the skirt. The teeth are preferably formed about only a portion of the circumference.

The indicator member 60 includes a plurality of indentations 68 formed about the outer circumferential surface of the skirt 74. The cap member includes a pair of upwardly extending resilient indexing members 22, each having an end portion that engages one of the indentations so as to releasably engage the indicator member and prevent rotation therebetween. The angular distance between the indentations 68 is substantially the same as the angular distance between the plurality of indicator member teeth 66. In this way, the indexing member selectively engages the next indentation upon each incremental advancement of the indicator member defined by the distance between adjacent teeth.

Alternatively, the indentations and indexing member may be reversed, i.e., the indentations are formed about an inner circumferential surface of the cap member skirt and an indexing member depends downwardly from the indicator member in a void formed in the skirt of the indicator member.

As shown in FIG. 1, dosage indicia 72 in the form of numbers or color codings are provided on the top surface of the indicator member and are visible to the user through the viewing window 34 provided in the top of the cap member. One of the skill in the art should understand that other indicia indicating the number of doses remaining in or dispensed from the container would include, but not be limited to, various alpha-numerical characters, words, terms or phrases (such as "full" and "empty"), scales, grids, arrows, raised portions, indentations, color coding and segmentation, shading and like markings, or any combination thereof. For example, a segmented color grid 172 displayed in the viewing window (as shown, e.g., in FIG. 1) could turn from green, indicating a full container, to yellow, indicating an intermediate capacity, and finally to red, indicating an empty container. It should also be understood that the indicia can be formed integrally with the counter member, or applied thereto by means of paint, dye, etching, pad printing, hot stamping or adhesive labels. When using numerical indicia, the numbers can be arranged to go from 0 (or some beginning number) to the predetermined number of available doses such that a display of that number to the user indicates that the container is empty, or, conversely, to go from the starting predetermined number to 0 (or some ending number), which again indicates to the user that the container is empty.

In a preferred embodiment, the indicator member is made of acrylonitrile butadiene styrene ("ABS"), which is receptive to certain alternative processes of printing or applying the indicia, including pad printing and hot stamping. The cap member and base member are preferably made of a hard plastic material such as Acetel.

Referring to FIGS. 15-20 and 32, a drive mechanism is shown as including a drive assembly 80 disposed between the cap and base. The drive assembly includes a ratchet wheel 82 coaxially mounted to a drive member on an axle 84. The ratchet wheel, drive member and axle can be made separately, with the ratchet wheel and drive member then mounted on the axle, or all three parts can be integrally molded as a one-piece component. The drive assembly is preferably made of hard plastic material such as Acetel.

The ratchet wheel 82 includes a plurality of teeth 88 (preferably ten) formed around its periphery. Each of the teeth includes an engagement surface 89 and a tapered surface 87. The drive member 86 includes a single tooth 81 extending radially from the axle 84. The drive assembly is mounted to the cap member by engaging opposite ends of the axle 84 with downwardly extending hub portions 36, 236 such that the axle, ratchet wheel and drive member rotate about an axis substantially perpendicular to the axial movement of the cap member relative to the base member and to the axis of rotation of the indicator member. Alternatively, the drive assembly can be mounted to the base member in a similar manner.

The drive mechanism further includes a pawl member 48, shown as a flexible rod or finger, which extends upwardly from the bottom portion of the base member and selectively engages one of the teeth of the ratchet wheel. Alternatively, the pawl member can be moveably secured to the cap member and extend through the base member to engage the top of the container, such that the axial movement of the cap member toward the container causes the pawl to move toward the ratchet wheel and engage one of the teeth thereon as described below. A non-return member 238, also shown as a flexible rod or finger, extends downwardly from the top portion of the cap member and selectively engages another of the teeth 88 of the ratchet wheel. It should be understood that the pawl member could alternatively extend from the cap member (and the non-return member from the base member) when the drive assembly is mounted to the base member, as described above.

In operation, as shown in FIGS. 15-18 and 32, the user depresses the cap 220 member from a fully extended position (see FIG. 15) toward the base member such that the cap member bottoms out in the base member at the bottom of the stroke (FIG. 16) and such that the base member imparts an axial load on the container until a metered dosage is dispensed therefrom. In a preferred embodiment, the biasing force of the spring 100, or alternative return mechanism such as the resilient arm members which act as springs, is less than the biasing force of the spring located in the metering valve of the container, such that the cap member first bottoms out in the base member with the container then being moved downwardly in the housing until a metered dose is dispensed.

Figure 15:
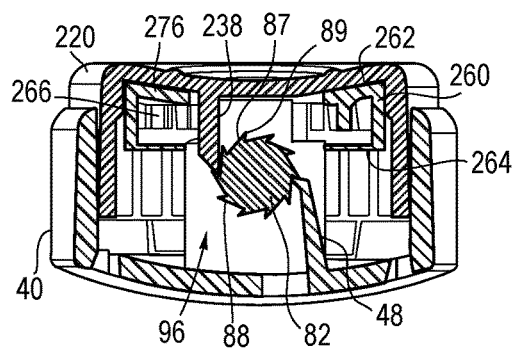
FIGS. 15-18 are cross-sectional views of one embodiment of a mechanical dose counter being actuated.
Figure 16:
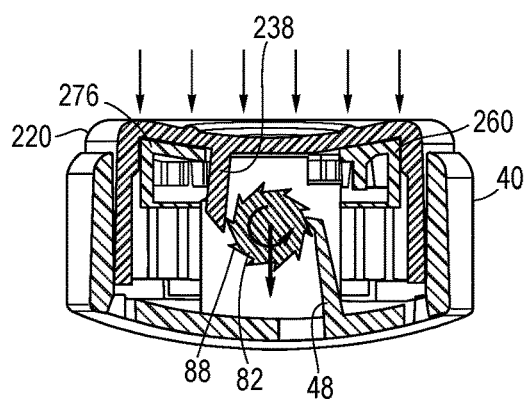
Figure 17:
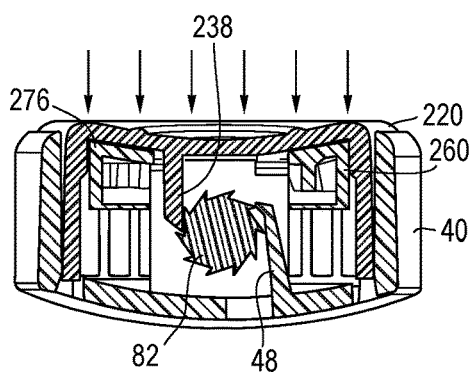
Figure 18:
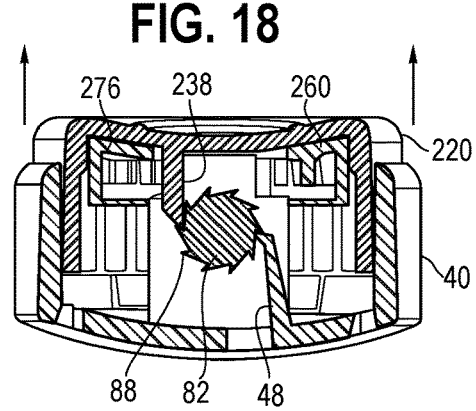

Referring to FIGS. 15-17, as the cap member 220 is depressed toward the base member 40, the pawl 48 selectively engages the engagement surface 89 of one of the ratchet wheel teeth and rotates the ratchet wheel. The tapered surface 87 of one of the teeth formed on the ratchet wheel simultaneously biases the non-return member 238 outwardly until it selectively engages the next tooth near the bottom of the stroke. The user then releases the cap member whereinafter the spring 100, or similar return mechanism, biases the cap member 220 away from the base member 40 until the engagement member engages the base portion at the top of the stroke as shown in FIG. 18. When the cap member is released by the user, the container is biased upwardly within the housing along the longitudinal axis such that the valve stem is moved to the closed position within the container. Simultaneously, as the cap member is released and allowed to move away from the base member, the pawl 48 is biased outwardly by the tapered surface 87 of one of the teeth on the ratchet wheel as the non-return member 238 prevents a backwards rotation thereof so as to maintain a unidirectional rotation of the ratchet wheel. At the top of the stroke (shown in FIG. 18), the pawl 48 is again placed in position for selective engagement with one of the teeth of the ratchet wheel. In this way, the ratchet wheel 82, and connected drive member 86, are advanced an incremental amount for every actuation of the container and the attendant release of medicament. The incremental amount is defined by and dependent on the number of teeth formed about the periphery of the ratchet wheel. When formed with ten teeth, as shown in the preferred embodiment, the ratchet wheel will make one full revolution for every ten actuations of the indicator device and container, or a tenth of a revolution for each actuation. One skilled in the art will appreciate that the ratchet wheel can be provided with various numbers of teeth formed about its periphery such that the more or less axial movements or actuations of the container are required to make one full rotation of the ratchet wheel. As can be appreciated the various movements of the ratchet and indexing portions of the drive and non-return mechanisms make various clicking noises during each actuation of the dose counter.

As noted, the mechanical dose counter or TMAI 6, and in particular the base 40, is attached to the top of an MDI, or bottom 14 of the container 12, in one embodiment and forms one half of the user interface of the MDI when integrated. The TMAI 6 is affixed to the MDI canister via a polymer label that is wrapped around both devices as shown in FIG. 1.

In one embodiment, an integrated dose indicator includes an electronic module 4 that may be combined with the mechanical dose counter, e.g., the TMAI 6, and may be mounted to the bottom of the TMAI via a fastening system such that the TMAI and electronics module become an assembly. Various fastener systems, or attachment devices, may include a modification of the bottom of the TMAI defining an extension, such as a circumferential skirt, that would house and contain the EM. Other attachment methods may include adhesives that to permanently or releasably attach the EM to the TMAI. The final eTMAI assembly would then be attached to the MDI for example with a polymer label wrap 600, 1600, 1602 as shown for example in FIGS. 6, 7, 41A and B, and 42A and B. To ensure that the EM is suitable for label wrapping, the existing method use to connect the TMAI to the MDI, the integrated TMAI and EM should have a maximum diameter no larger than the TMAI alone. Additionally, it may be desirable for the EM to be as short as possible (in the longitudinal direction) thus adding as little height as possible to the final integrated assembly. By minimizing the height increase of the overall assembly, and the distance between the actuation surfaces of the top of the TMAI and the bottom of the housing 200, the addition of the EM does not adversely affect the usability of the existing MDI. As mentioned above, the EM preferably remains within a maximum diameter defined by the diameter of the existing MDI canister and TMAI. Thus the height, which is preferably minimized, combined with the diameter maximum, defines the available volume and cylindrical shape to that volume within which the EM must be configured, as shown for example in FIG. 2.

Figure 3:
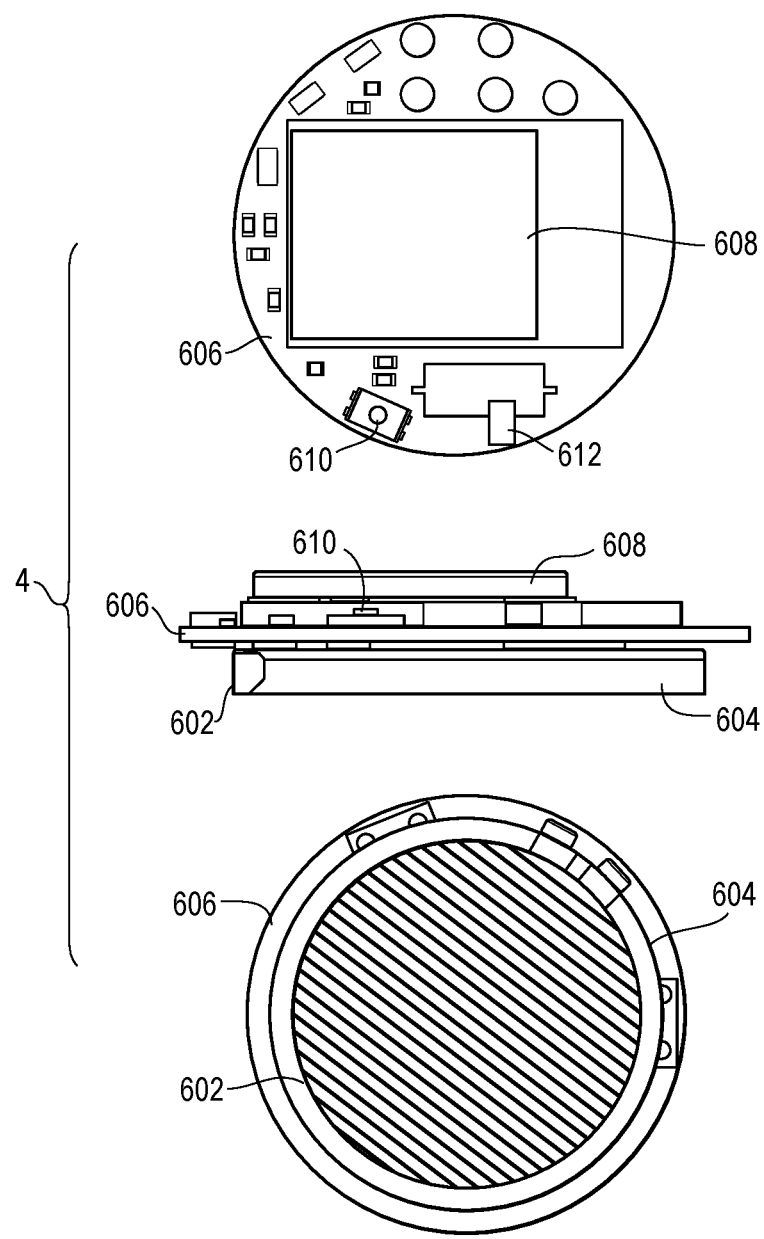
FIG. 3 are views of the electronic module.
Figure 28:
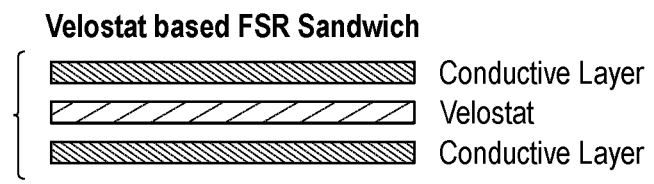
FIG. 28 is a force sensitive resistor sensor assembly.

Referring to FIGS. 3, 5 and 28, the electronic module may include one or more of the following elements:
1. Force sensor 602 for detecting the force applied to the system via the user's applied force to the top of the TMAI
2. Li-Ion Coin cell battery 604
3. Printed circuit board assembly (PCBA) 606
4. Bluetooth Low Energy module/transceiver 608 (e.g., Nordic chip)
5. LED 610
6. On/off switch 612

7. Infrared LED and Phototransistor (IR LED & PT)
8. Microcontroller (within BTLE SoC)
9. Accelerometer Electronic Module (EM) Description:

The EM registers an actuation when the MDI (and mechanical dose counter) are actuated (date and time) and stores this information. A wireless radio may be incorporated into the EM so that the actuation data stored in the device can be communicated to another device, preferably a smart phone where the data can be analyzed, processed, and presented to the patient or health care provider in a meaningful way via a software application (app), as shown for example in FIGS. 30 and 31. The EM may be affixed to the bottom of the TMAI, which may necessitate slight modifications to the TMAI but otherwise would leave the TMAI counter mechanism unchanged. In this way, the EM may be incorporated into existing MDI and TMAI systems, or provide for retrofitting such systems, such that proven TMAI mechanical dose counters do not need to be modified in any significant way in order to add the EM functionality. As well, manufacturing may be simplified by adding the EM module as a subassembly step without extensive alteration of the existing TMAI assembly process.

During operation, the user applies the actuation force to the top of the TMAI and the bottom of the MDI, which forces displacement in both the TMAI and MDI mechanisms. This is required for both devices to operate, i.e., for the TMAI to count and the MDI to release a dose of medication, as shown in FIG. 3.

Figure 45:
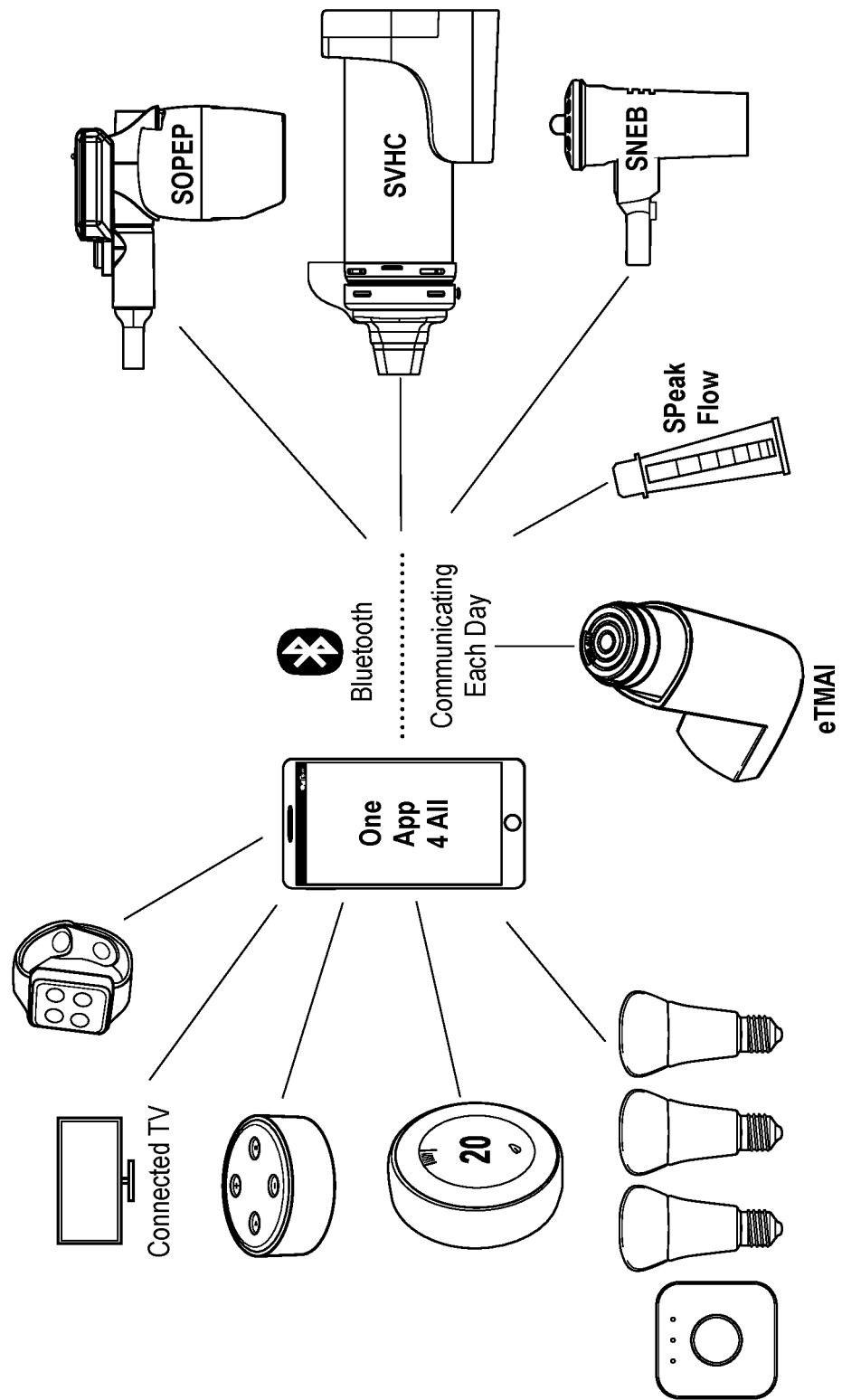
FIG. 45 is a schematic view showing communication between various smart devices.
Figure 46:
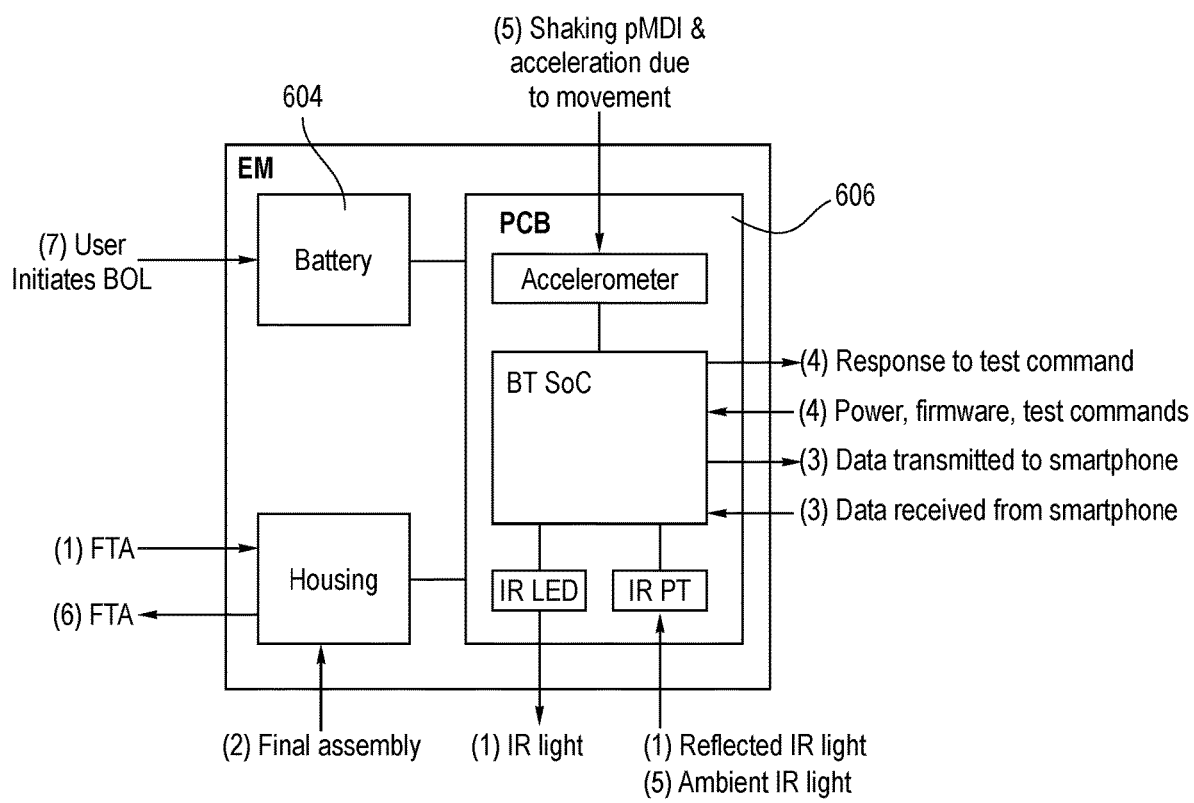
FIG. 46 is a schematic showing the electronic module architecture.
Figure 47A:
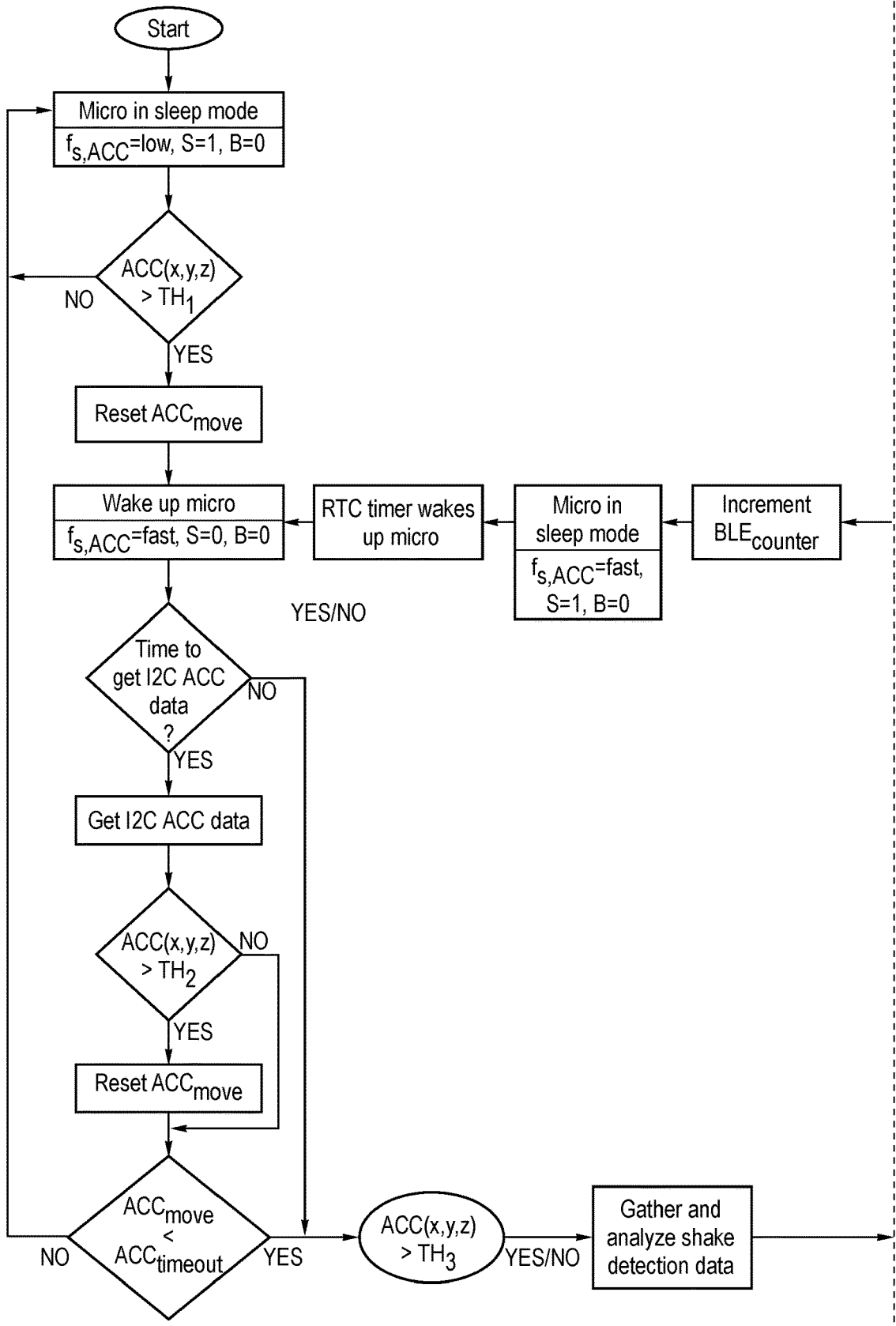
FIG. 47 is a flow chart showing the operation of one embodiment of the system.
Figure 47B:
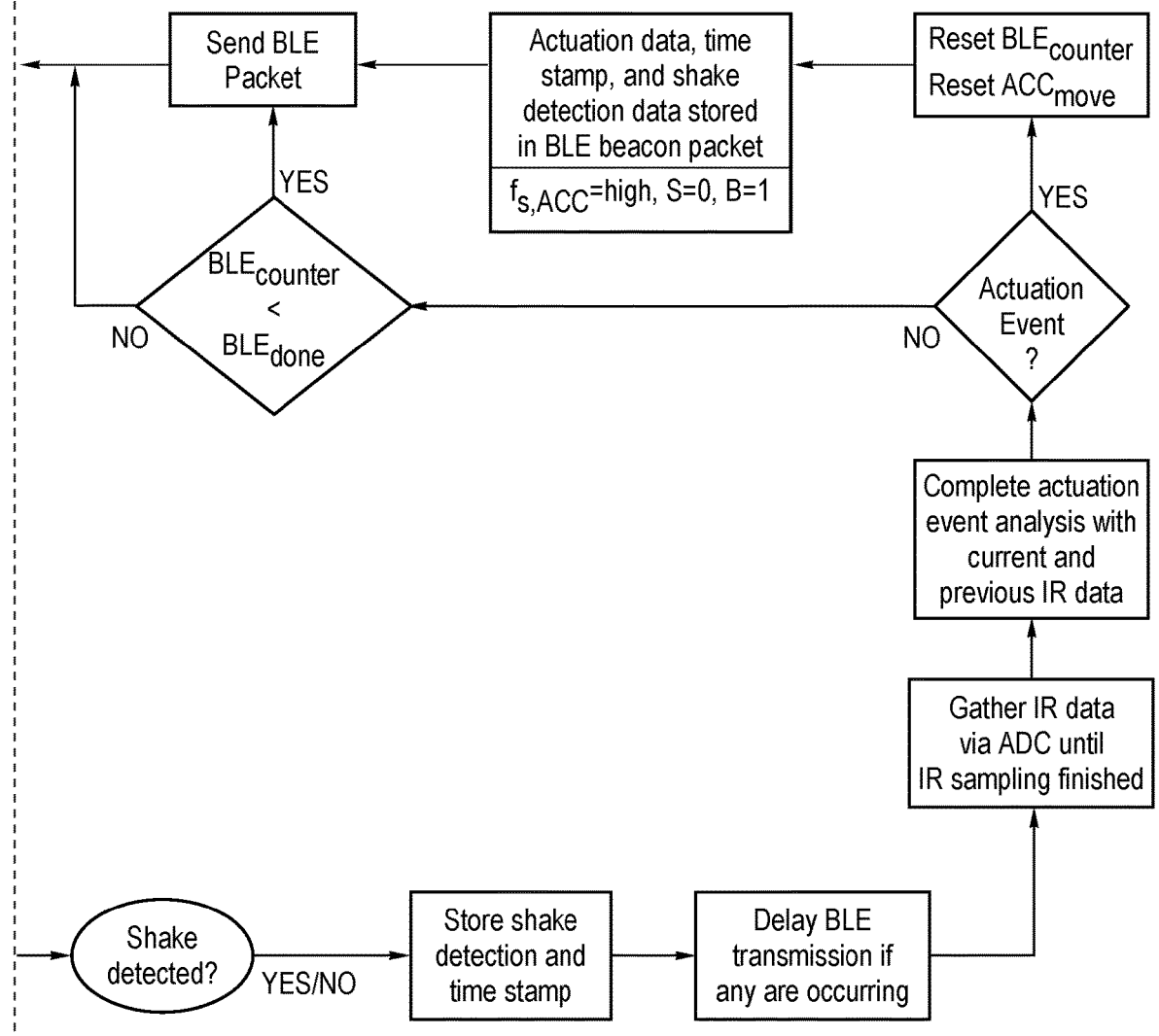
Figure 48:
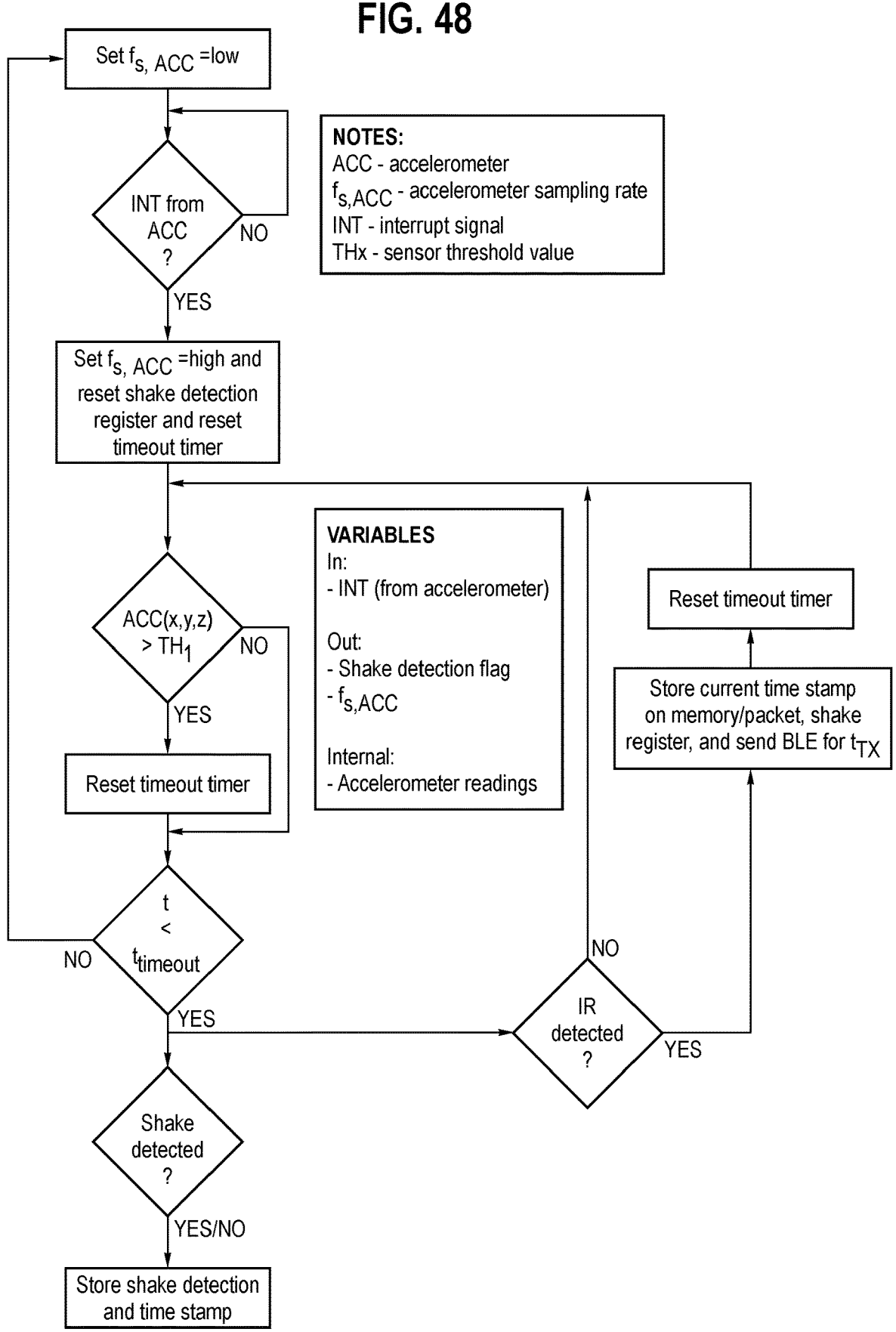
FIG. 48 is flow chart showing the Accelerometer and Wake/Shake Detection Logic.
Figure 49:
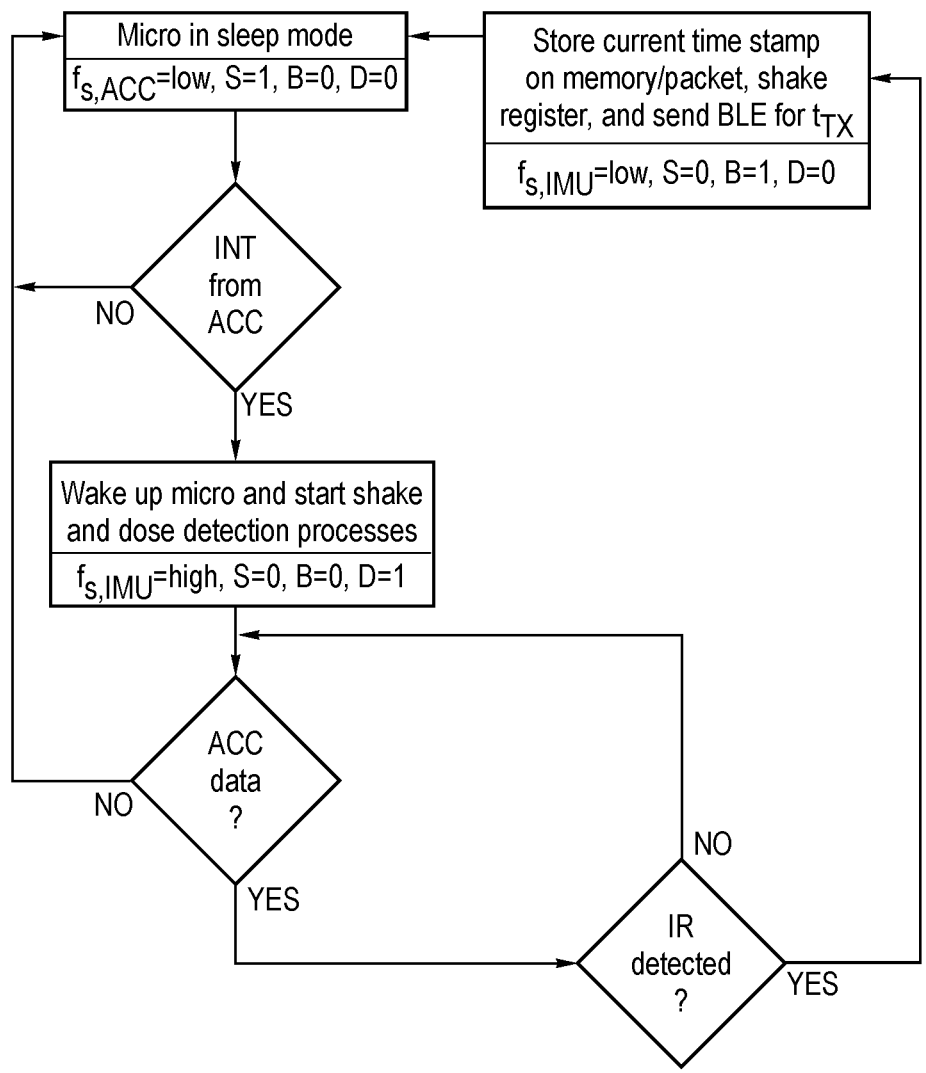
FIG. 49 is a flow chart showing the Microcontroller Logic.
Figure 50:
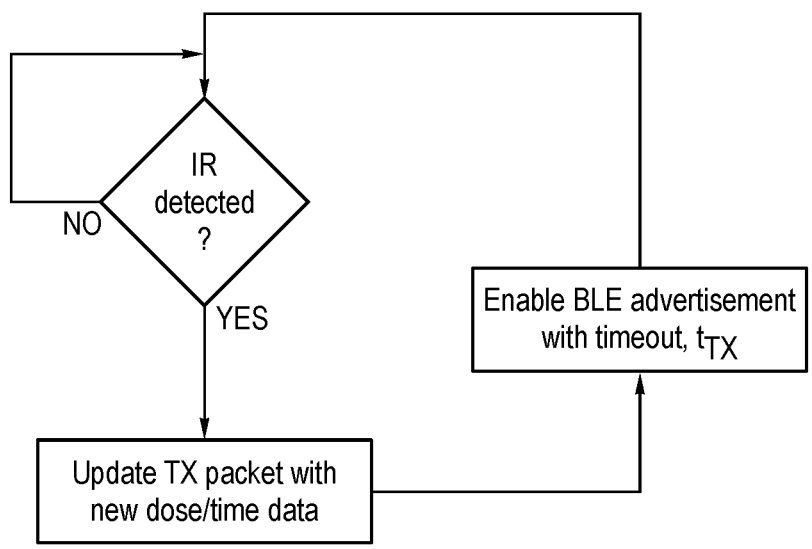
FIG. 50 is a flow chart showing the Bluetooth and Advertisement Packet Logic.
Figure 51:
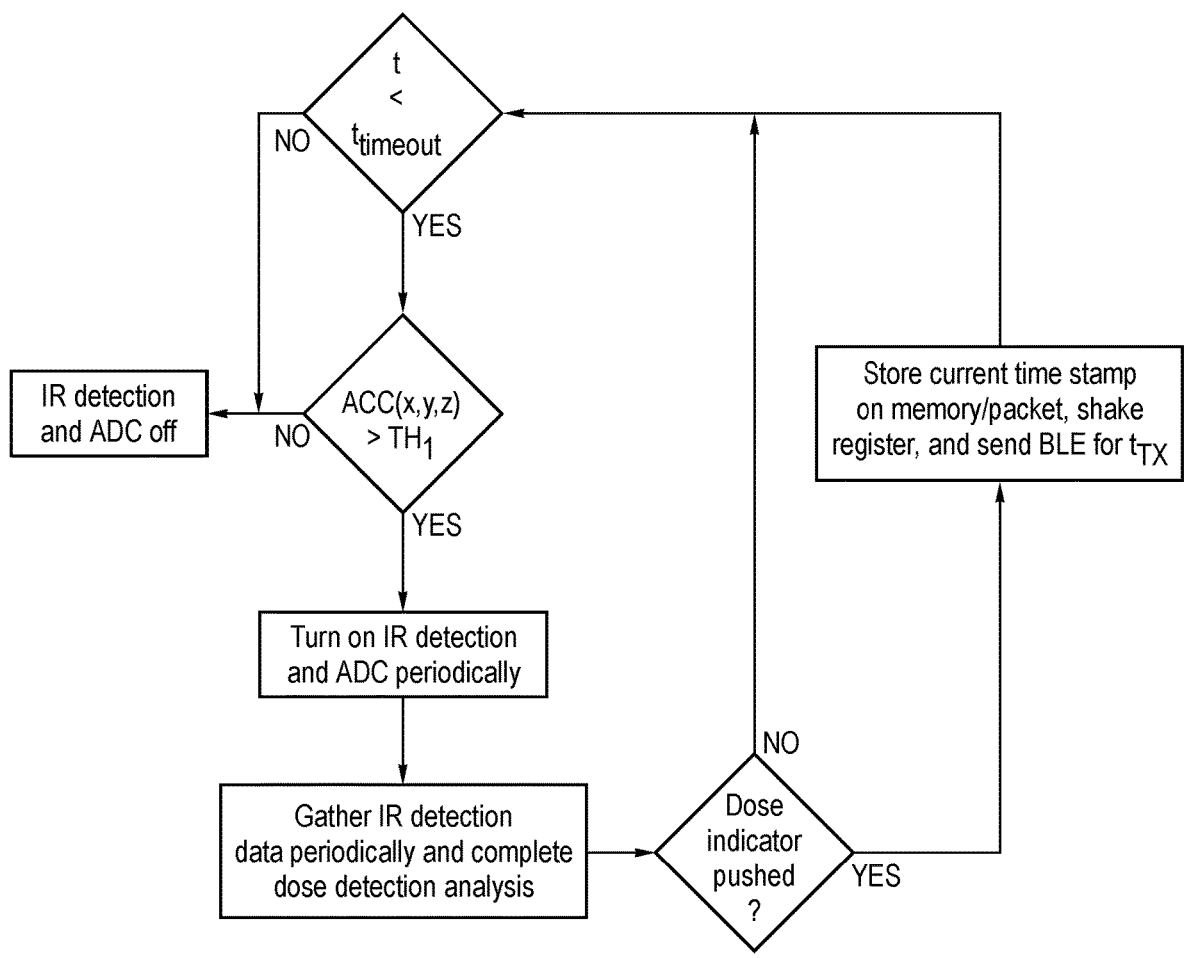
FIG. 51 is a flow chart showing the IR detection an ADC block logic.
Figure 52:
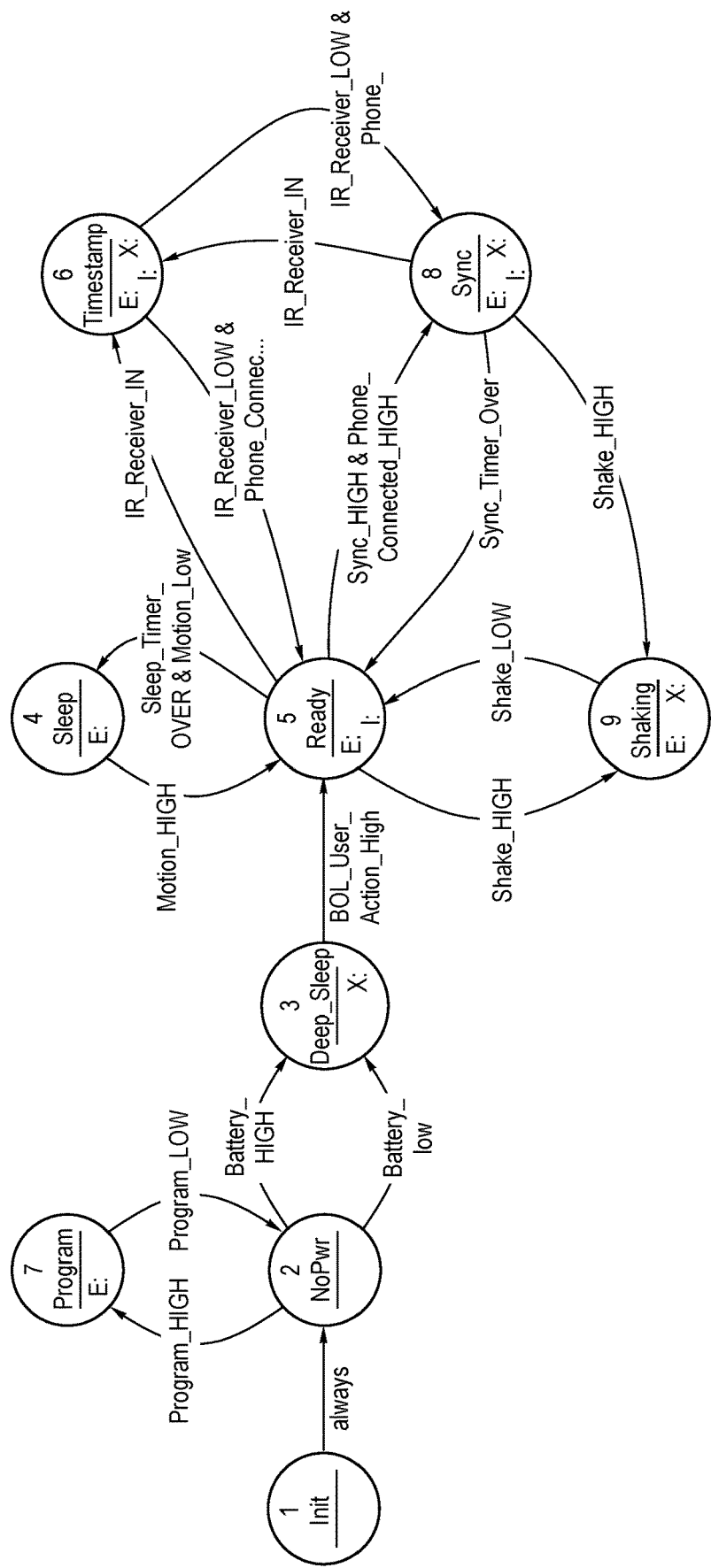
FIG. 52 is a schematic showing the finite state machine logic for the system.

The EM would receive the applied forces directed to it via the bottom of the TMAI and the top of the MDI, and the container in particular. In one embodiment, the force sensor may be configured as force sensitive resister (FSR) type sensor 602 which changes electrical resistance in response to pressure applied to the sensor. There are various suitable types of FSR sensors, with one preferred embodiment using a pressure sensitive conductive sheet (Velostat), shown in FIG. 28. FSR's are one embodiment of a preferred sensor configuration due to their low power consumption requirements. Due to the limitations on packaging (size) and cost, low power consumption is one consideration. Configured correctly within the design, a Velostat based FSR would be very low cost which would be advantageous over other more costly FSR type sensors. In this application, the Velostat material would be incorporated into the design between two conductive layers to form a sandwich. This sandwich would in effect form to the FSR as shown in FIG. 28. Alternate FSR's can be used including one configured as shown in FIG. 5, including an active area 302, a plastic spacer 304 and a conductive film 306. It should be understood that other force sensors may be used and are suitable for integration into the EM, including without limitation resistive, capacitive, piezo, load cell and/or Micro-Electro-Mechanical System MEMS force sensors, and/or combinations thereof. Referring to FIG. 45, in one embodiment, the eTMAI includes an EM and a TMAI architecture with various inputs and outputs, including BOL (beginning of operating life), FTA (Force to Actuate a TMAI, and FTF (Force to Fire a pMDI) inputs.

Battery:

In one embodiment, the battery 604 in the EM may be a standard Coin Cell Lithium Ion (Li-ion) battery. Coin cell Li-ion batteries are readily available in volume quantities in configurations that are suitable to this application, and therefore provide lower cost battery options available for portable electronics. Secondly, coin cell Li-ion batteries have the energy storage capacity that is well suited to this application. Thirdly, the coin cell batter has a disc shape that is suitable for integration requirements. For example, the coin cell batteries may be configured in cylindrical formats in diameters matched to the TMAI and EM. In this way, a coin cell Li-ion battery may be selected that is as large as possible within the constraints of the maximum diameter defined by the TMAI/MDI so as to get maximum storage for the lowest possible height. The outside diameter of the TMAI/MDI Canister is normally between 22 mm and 24 mm. One specific battery that suits this application is the CR2012 (20 mm diameter, 1.2 mm height, and 50 mAh capacity). At 20 mm in diameter, the battery fits within the 22 mm diameter constraint of the TMAI/MDI canister leaving enough room for plastic walls to contain the assembly in the final configuration. This allows for label wrapping of the overall TMAI-EM assembly; the method currently used by manufacturers to couple the existing TMAI to the MDI canister.

Figure 41A:
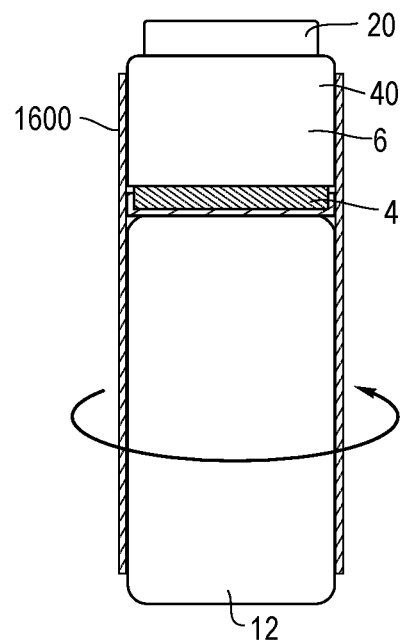
FIG. 41A is a cross sectional side view of another embodiment of a mechanical dose counter and electronic module applied to a medicament container.
Figure 41B:
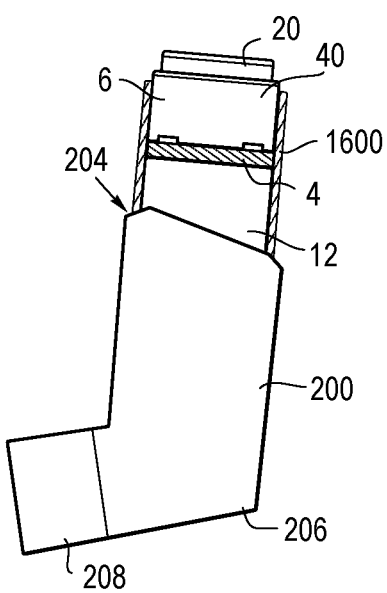
FIG. 41B is a partial cross sectional side view of the mechanical dose counter and electronic module applied to the medicament container in a metered dose inhaler assembly.
Figure 42A:
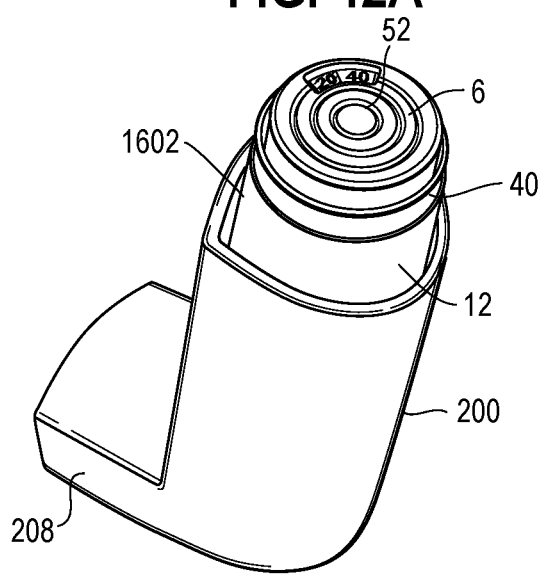
FIGS. 42A and B are top perspective and partial cross sectional side views of one embodiment of pressurized metered dose inhaler.
Figure 42B:
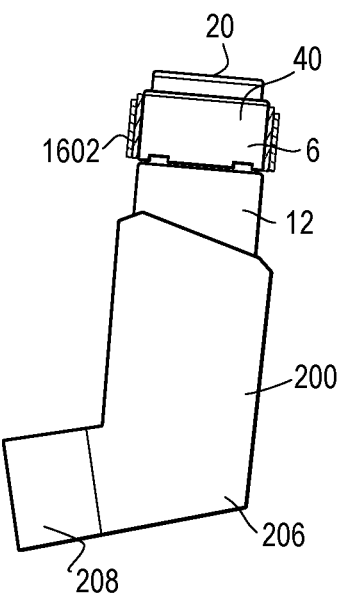

In an alternative embodiment, shown in FIGS. 41A and B and 42A and B, the battery 1600, 1602 is configured using imprint flexible battery technology that makes ultrathin, flexible, printed batteries. The battery 1600, 1602 may be configured as an imprint flexible 360° wrap around battery. The battery may be wrapped around the canister 12 like the label 1600 that attaches the eTMAI, 4, 6 to the container, or the battery wrap 1602 may be wrapped around the eMTAI components 4, 6 only and then covered by a label 600 connecting the dose counter to the container.

Bluetooth Low Energy Transceiver:

Cost and size are similarly important in selecting an embodiment of the wireless transceiver 608 to be able to communicate with a Smartphone or tablet. As with selection of the sensor to detect actuation, low power consumption is a consideration in selecting the transceiver, together with the overall size or footprint to ensure that overall size of the package is minimized. One suitable embodiment uses a nRF24L01P 2.4 GHz Bluetooth Low Energy (BLE) transceiver 700 selected for low power consumption and minimal packaging dimensions for integration into the overall PCBA. While a BLE transceiver with only transmission capabilities is suitable for certain applications, it should be understood that a transceiver with both transmission and receipt capability may also be suitable for other applications, for example where communications initiated from the Smart phone could enable certain functionality of the EM.

LED:

A light emitting diode 610 is configured to provide some feedback to the user about the operation of the EM. Although in one embodiment the operation of the EM, in terms of the integration of the Metered Dose Inhaler would be not observable, feedback is considered as valuable for a number of purposes. In one embodiment the LED would be behind the label overwrap 600 used to connect the TMAI/EM sub assembly to the MDI canister. The labels may include polymer labels that have the appropriate strength and durability characteristics to suitably maintain connection of the devices during use, but are also translucent and may permit light from an LED to be seen by the user through the label. As such, while no further customization of the integrated device is required, a convenient and low cost means of communicating information to the user is provided. The information that may be communicated may include confirmation that an actuation has been recorded, confirmation of operation, confirmation of communication or connection with a smart phone, and trouble-shooting diagnostics information in the case there is a problem. Other information about the operation of the EM, including information that the EM is detecting, storing and communicating, may also be considered. For example, the EM, via the LED, may assist the user in locating their inhaler when it is misplaced or when it is dark.

Figure 40:
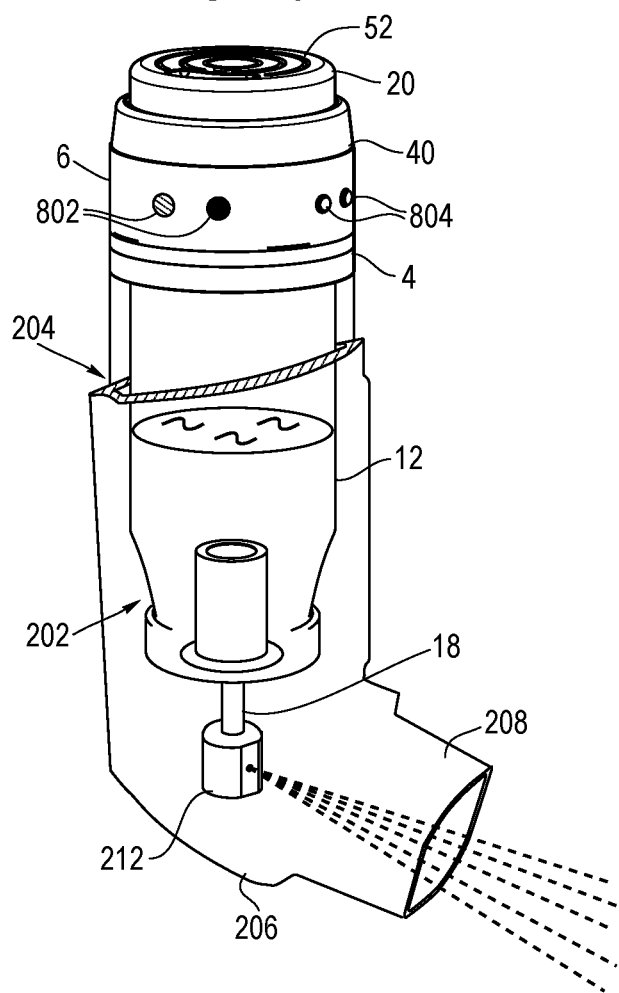
FIG. 40 is a partial cross sectional view of another embodiment of a mechanical dose counter and electronic module applied to a metered dose inhaler.

Referring to FIG. 40, the EM or eTMAI may be configured with various feedback devices and system, including for example indicator lights 802 (e.g., red and/or green LED's), that may be programmed to illuminate in response to various inputs. In an alternative embodiment, the outer casing may be made of glow in the dark materials to help user find the inhaler in low light situations. Alternatively, the device may include an ambient light sensor, such that when it is a low light, or no light, the eTMAI would periodically pulse an LED to indicate location such that the user may locate the device in a dark room. For example, the system may provide a pulse every 3 to 5 seconds, or the frequency may be programmable by the user depending on preference.

On/Off Switch:

A switch 612 is provided that allows for the module to be turned off to conserve power. Other power control systems may be suitable, for example by remote actuation, to put the device to sleep or awaken the device, for example using an accelerometer.

Figure 33:
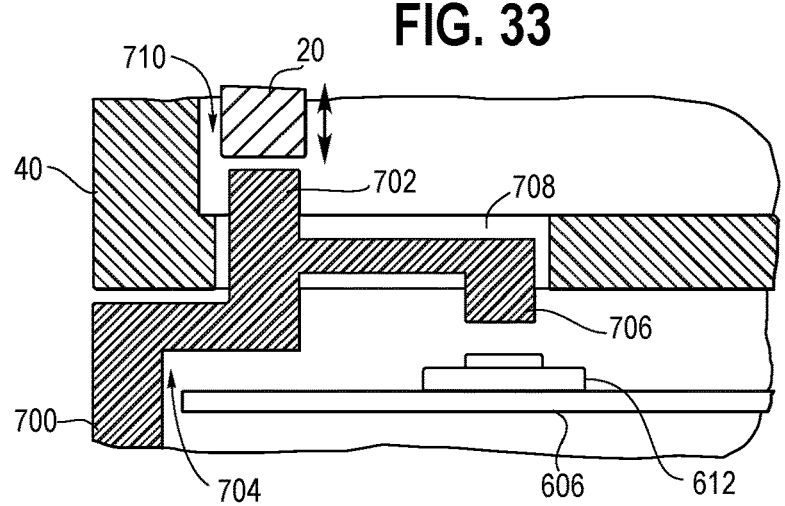
FIG. 33 is a cross-sectional view of one embodiment of a wake-up switch.
Figure 34:
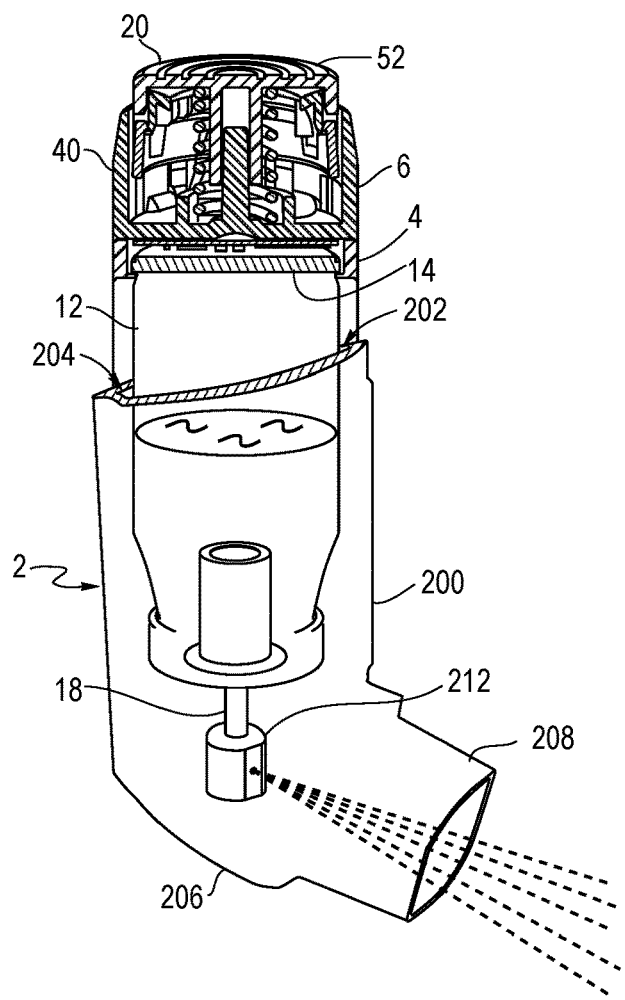
FIG. 34 is a partial cross sectional view of one embodiment of a mechanical dose counter and electronic module applied to a metered dose inhaler.
Figure 35:
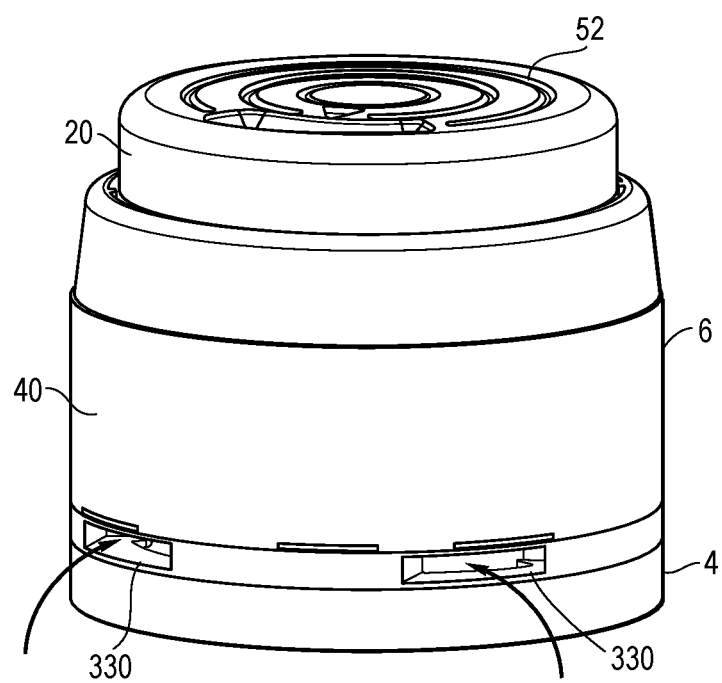
FIG. 35 is a side perspective view of one embodiment of a mechanical dose counter and electronic module.
Figure 36:
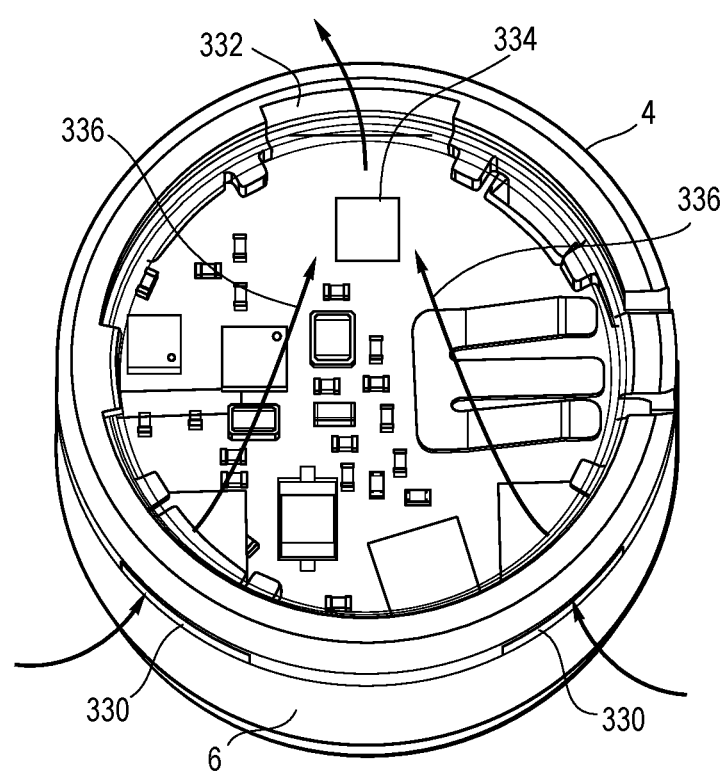
FIG. 36 is a bottom view of the mechanical dose counter and electronic module shown in FIG. 35.
Figure 37:
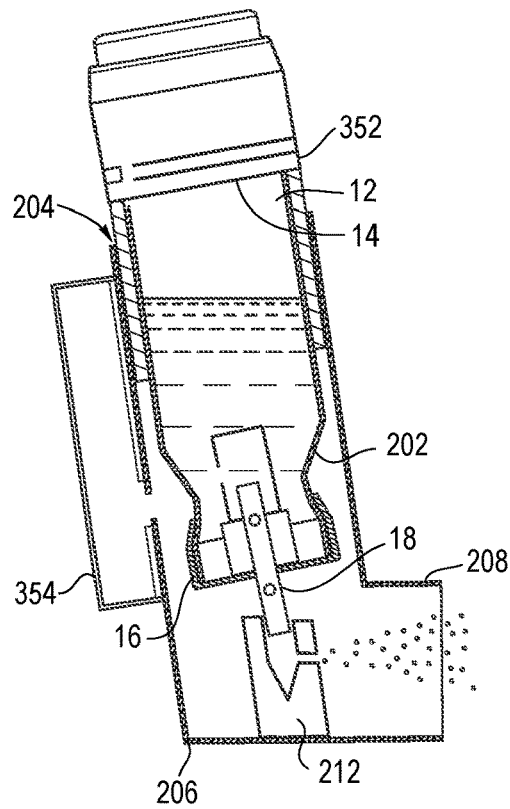
FIG. 37 is a partial cross sectional view of another embodiment of a mechanical dose counter and electronic module applied to a metered dose inhaler.
Figure 38:
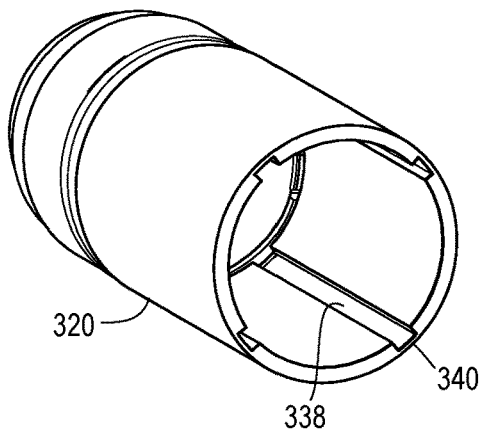
FIG. 38 is a side perspective view of another embodiment of a mechanical dose counter and electronic module.
Figure 39:
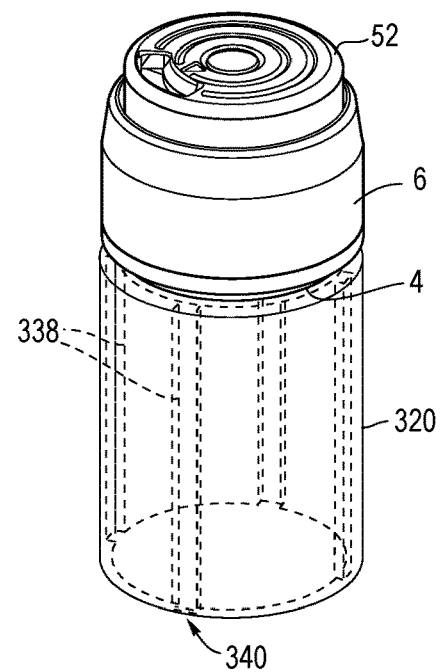
FIG. 39 is a bottom perspective view the mechanical dose counter and electronic module shown in FIG. 38.

Referring to FIG. 33, one embodiment of a waking up device may accommodate a first time use only at the priming stage, and waking up the device from deep sleep by using a tactile switch 612. Counting thereafter is performed using the same switch 612. In one suitable embodiment, the tactile switch 612 may be a TL3780 Ultra Miniature. The switch is configured in normally open ("NO") configuration. A PCBA 606 is mounted on the underside of the TMAI. A cantilever arm 700 is molded as part of the eTMAI carrier component, contoured to the cylindrical shape. The arm functions as lever, which pivots about a fulcrum 704 defined at the main junction to the base. A force is applied by the cap 20 rim to an engagement pad 702 on the cantilever spaced from the fulcrum 704, with an opposite end of the arm 706 engaging the switch positioned on the surface of the PCBA facing the base. The switch 612 is shaped and dimensioned to fit in an enlarged cutout 708 defined by the base near an orientation paddle. The engagement pad 702 of the cantilever arm extends upwardly into an interior space 710 of the TMAI to engage with the rim of the cap. Any over travel of the cap 20 is accommodated by compliance in the bending of the cantilever arm 700. The initial closing of the switch during a first priming shot may bring the processor out of a deep sleep state. Thereafter, the actuation of the TMAI is counted by this same switch.

Description of Principles of Operation:

The EM may be integrated with existing mechanical TMAI designs and their manufacturing processes. In one embodiment, the EM may be added as a simple subassembly step with straightforward attachment means. What enables this is that fact that the EM detects the actuation event via a force sensor. Similarly, the mechanical TMAI is essentially a mechanical force sensor. When a predetermined force is applied, the mechanical TMAI advances and registers that an actuation of the MDI has occurred. Similarly, the EM detects an actuation when a predetermined force has been applied, only in this case it uses electronic means for detection. By using the same methodology, it allows the two devices to be "stacked," or arranged serially, which allows for a simplified integration.

In operation, the applied force generated by the user's finger is applied to the top of the TMAI which is then directed through the TMAI, through the EM, and then to the MDI Canister, or container. It is important to note that in this stack, i.e., serial arrangement, direct communication of forces into each component ensures stability of the mechanical contact between the EM and both the TMAI and MDI canister. This will provide precise and consistent force transfer and therefore reliable detection of the force event by the EM.

One component that to consider in this configuration is the label wrap 600 that is intended to connect the TMAI-EM assembly to the canister. Although the stack of the TMAI-EM and MDI canister will have negligible compression, the assembly should ensure that the label wrap does not introduce variability to the ability of the EM to detect a force event. The FSR used in this embodiment is selected not only for cost and integration benefits, but also because it has negligible compression. Label materials in general are highly compliant and as such, even when the label is applied, it will not appreciably interfere with the ability of the force sensor to detect the force event.

Figure 6:
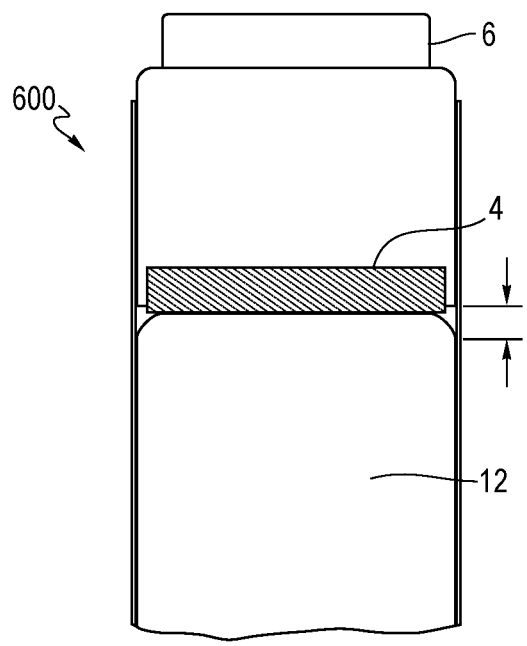
FIG. 6 is a side view of one embodiment of a mechanical dose counter and electronic module applied to a metered dose inhaler.

Additionally, the connection system between the EM and the TMAI should be configured to ensure proper force transfer and registration. Forces must be allowed to transfer cleanly from the users finger, through the TMAI, through the EM, and then to the canister. In a preferred embodiment, the bottom of the TMAI is modified to include a cup adapter into which the EM is pressed. Snap fits may be used to capture the EM but other methods, as disclosed above, may be used including adhesives, tapes, etc. The extension on the bottom of the TMAI may provide extended surface area to which the label could be applied which ensures a seamless integration with the MDI canister and minimal gaps which could cause creases which would be visible to the user. However, in one embodiment, the extension does not come into contact with the top of the MDI canister so as to ensure there is no force transfer between the TMAI directly to the canister, but rather is directed through the EM so as to avoid any bypass of the EM and thereby prevent the EM from detecting the force event. In one embodiment, a skirt extends down from the top of the TMAI but a gap remains between the TMAI skirt and the MDI canister in the final assembled state with the EM. This would ensure that the forces are directed from the TMAI, through the EM, and into the MDI canister and not through the skirt extension, as shown in FIG. 6.

Figure 7:
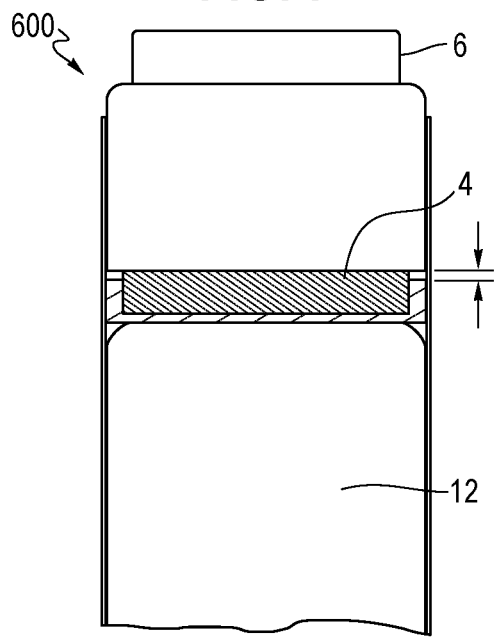
FIG. 7 is a side view of one embodiment of a mechanical dose counter and electronic module applied to a metered dose inhaler.

In an alternate embodiment, the arrangement may be inverted and a separate adapter component could be used to house the EM as shown in FIG. 7. In this embodiment the stack would be such that this adapter would directly contact the top of the MDI canister and the EM would sit inside it. The TMAI would then sit directly on top of the EM. In this embodiment, a gap is required between the adapter and the TMAI, similar to the gap described above with respect to the embodiment of FIG. 6. Various connection systems may then be used to couple the EM to the TMAI, for example with snap fits, adhesives etc., as shown in FIG. 7.

In operation, and referring to FIGS. 47-52, the EM would electronically register each actuation once a predetermined force is applied to the force sensor. A microprocessor would monitor the force response of the force sensor and determine when an actuation has occurred. When an actuation is registered it will be stored into memory. When connected to a smart phone, packets of information representing, at a minimum, the actuation registered and its corresponding time and date would be sent. The EM could also have a decrement counter that continually updates and subtracts actuations so that an accurate "doses" or "counts" remaining is calculated. This information can also be sent to the connected device. Referring to FIGS. 21-23, 27 and 47-52, the operation of the device and system is shown.

Other Alternate Embodiments

Alternate Locations for EM:

The EM may operate as a dose counter or tracker in many different configurations, with or without being integrated with the TMAI. In one embodiment, shown in FIG. 8, the EM 4 may be configured to be integrated with the top of the TMAI instead of the bottom. In this configuration, the users finger would contact the top of the EM instead of the TMAI and thus the actuation force would be directed through it into the top of the TMAI. There are other mechanical considerations with this embodiment that would need to be considered including that the EM defines the user interface and must therefore be suitable to be touched by the users finger. In addition, any mechanical counting displays on the top of the TMAI would have to be visible and so not blocked or hindered by the addition of the EM, for example by providing a viewing window in a side wall of the TMAI, with an indicator and indicia visible therethrough.

Figure 9:
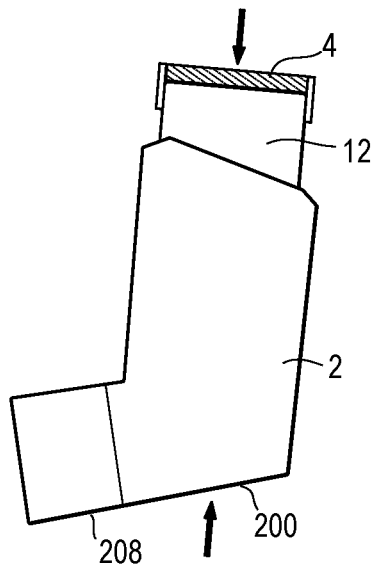
FIG. 9 is a side view of one embodiment of an electronic module applied to a metered dose inhaler.
Figure 10:
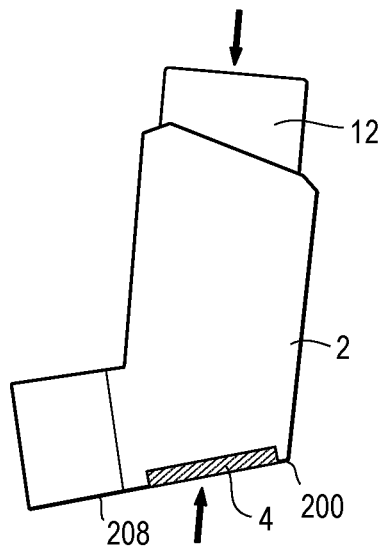
FIG. 10 is a side view of one embodiment of an electronic module applied to a metered dose inhaler.

In another embodiment, the EM may be a standalone dose counter or tracker on its own, exclusive of any mechanical device. The low cost and slim integration that make the EM suitable for integration with a mechanical dose counter is also advantageous in a standalone configuration. In this embodiment, the EM may or may not add a display element which would communicate directly to the user the number of actuations remaining, as do mechanical dose counters. When configured without a display element, the EM may instead communicate the dose or count status and tracking information through a smart phone. Integration of the EM to the top of the MDI canister may be required so that, like the earlier embodiment, it forms a suitable user interface for the user's finger. Attachment of the EM to the MDI canister may be achieved in a number of different ways including via adhesives or the addition of an adapter component that will house the EM and also facilitate attachment to the MDI canister, for example a friction fit collar or combination with other attachment means, as shown in FIG. 9.

In another embodiment, the EM may be attached or integrated with the actuator portion of the MDI, or a bottom of the actuator housing. As a low cost force based counter/tracker, the EM may be well suited to being added in this configuration as it would require very little modification to the existing and well proven MDI platform. Like the earlier embodiment where it is attached to the MDI canister, in this configuration the EM may also have a display to communicate doses remaining or tracking information but similarly may not incorporate a display or screen, but instead rely on the screen of the smart phone or connected device. Attachment to the bottom of the MDI actuator may be carried out in a number of standard ways including snap fit, press fit, adhesive, etc. As in other embodiments, the bottom of the EM would become part of the user interface where the use applies the actuation force.

Alternate Embodiments—Alternate Count Detection Method—Infrared Sensor Displacement Sensor Like the force sensor described in the preferred embodiment above, whatever actuation detection method used preferably has low power consumption, low cost, and very small overall packaging. An alternate method that satisfies these requirements incorporates an Infrared LED 620 and sensor 622 to detect the displacement of the internal TMAI components. Although the TMAI is a force based counter, it still requires displacement to actuate and achieves a very accurate and consistent displacement to actuate. In one embodiment, the infrared LED and sensor would reside on the EM where the EM would have a similar overall shape and size to the one disclosed above with a force sensor. In this embodiment however, instead of a force-based methodology for detecting actuation events, it would depend on displacement of the TMAI mechanism, i.e., include a displacement sensor. In this embodiment, the EM would be similarly situated between the bottom of the TMAI and the top of the MDI canister. An infrared LED and sensor would be configured to be directed up and inside the TMAI mechanism where the infrared LED 620 could illuminate features within the TMAI mechanism. The LED light would shine vertically up into the TMAI and the sensor 622 would sense or read the light bouncing back as shown in FIG. 11, with the operation disclosed in FIG. 51. The displacement sensor may also be disposed between a base and cap of the TMAI. It should be understood that other types of displacement sensors besides the infrared LED and sensor may be suitable, for example various proximity switches. Conveniently, the bottom of the TMAI may already have a number of holes or openings 624 to allow for manufacturing and molding. These holes or openings 624, or new holes, may be used to allow the LED and sensor to access the internal mechanism and detect the movement of one or more components of the mechanism. Detection may be done by sensing the movement of existing features within the TMAI mechanism which may including any of the mechanical elements (cap, gears, supports, guiding features, etc.). Alternately, with minimal modification to the existing TMAI mechanism, the existing features inside the TMAI can be modified to enhance the ability and precision of the infrared sensor displacement detection. This may include optimizing the position and shape of the features as well as the colour or texture. Additionally, a feature may be added, for example a post with a flat top, that would have no impact on the TMAI mechanism but would optimize displacement detection of the infrared sensor and bring the mechanical features into closer range of the sensor. Other factors may also be identified for optimization with minimal effect on the basic TMAI mechanism. This may include ensuring that minimal ambient light intrusion occurs that may interfere with the ability of the infrared sensor to pick up the actuation event. The infrared sensor approach may offer some advantages over force sensing as it eliminates any integration with the MDI canister as mentioned above. All required interfaces to enable correct operation can be contained with the TMAI and EM. In operation, the EM would be programmed with a displacement that once exceeded by the TMAI, would register an actuation. For example, in one embodiment, the TMIA has approximately a 3.5 mm total travel from a nominal, at-rest position to being bottomed out at a maximum depressed position. The actuation point typically occurs about midway through the total travel. Alternate Embodiments—Alternate Count Detection Method—Infrared Sensor Displacement Switch The eTMAI and/or EM is configured such that it may provide various count detection methods and features, including; (1) Sound of aerosol "woosh" release from the canister picked up by the microphone inside eTMAI, recording an actuation count; (2) Flow of air in the airflow communicating channel picked up by the flow sensor, recording and actuation count; (3) Drop in pressure in the air flow communicating channel picked up by the pressure sensor, recording an actuation count; (4) Temperature sensor inside the eTMAI would take the temperature of the canister, which is much colder when actuated, it would indicate device was used, therefore record or verify an actuation count; (5) Microphone in the eTMAI picking up the signature click of the actuation rotating gears of a mechanical dose counter such as TMI dose counter etc.; and/or combinations of the various device and systems disclosed herein, which may improve the overall veracity of the system by verifying counts and thereby increasing the accuracy of the data captured and/or reported.

Alternate Embodiments—Alternate Count Detection Method—Infrared Sensor Displacement Switch An alternative displacement sensor includes many of the same features as the displacement sensor disclosed above that incorporates an infrared LED and sensor, but instead of measuring the amount of displacement and determining whether an actuation event has occurred when a predetermined displacement has been reached, the alternate embodiment may be used to configure the infrared LED light to be interrupted fully by a feature from the TMAI. In this configuration, which also is configured as a displacement sensor as shown in FIG. 12, the infrared sensor and detector would be arranged in a configuration where they were opposite each other. The LED would shine directly at the sensor. Actuation would be determined when a blocking feature 624 from the moving part of the TMAI breaks the light beam which would be detected by the sensor and determined by the CPU to be an actuation, or a measurement of a predetermined displacement has been satisfied. In this embodiment, which is directed to whether a threshold displacement has been reached, rather than measuring the displacement, the system does not need to detect specific displacements. In this way, the displacement sensor functions as more of a switch configuration (or absolute displacement), with the difference between not-actuated and actuated, in terms of sensed IR energy could be made to be quite significant and therefore may be more tolerant to sources of interference including outside light emissions. The blocking feature 624 is incorporated into the TMAI that is configured to break the light beam from the LED at a predetermined displacement that corresponds to the actuation point of the TMAI. Since the actuation point of the TMAI occurs at the mid-point of its total travel, provision for over travel of the added beam interrupter feature would have to be provided.

Other Alternative Sensors

Once an actuation is detected and stored by the EM, and referring to FIGS. 47-51, the EM may wirelessly transmit the time and day of the actuation(s) and the total number of button presses that occurred to the user's mobile device app.

Besides the force and displacement sensors disclosed above, other basic types of sensors, or combinations thereof, may also be suitable, with each sensor measuring one or more of the following: force, motion, sound, or distance to detect an actuation, e.g., a button press (downward push). For example, the motion may be sensed by an IMU sensor where it will detect the vibrations generated by a user button push as well as by the spring-like mechanical component that decrements the mechanical counter. Since the button push generates a clicking sound, this noise can be sensed by a MEMS microphone. In addition, the distance of the mechanical actuation, e.g., button push, may be detected by an IR emitter (LED) and detector (phototransistor) where it behaves like an IR proximity sensor, or displacement sensor, as described above.

In various embodiments, the eTMAI or EM may be configured such that provides the various sensing functions and features: (1) inhalation detection: by sound, flow, or pressure sensor, confirming the user inhaled correctly during the administration of the drug; (2) Inhaler Identification: identifying the type of drug being used, assembled at Pharma, programmed to drug type, including a module attached to canister and paired to the pMDI actuator, with the EM communicating with the pMDI actuator or vice versa; (3) Shake Detection: Accelerometer 900 shake detection sensor, monitors for shake event and/or effectiveness of shake for proper mixing of drug before use; (4) Actuation Detection via Canister Temperature: Temperature of canister would drop when actuated due to rapid expansion of propellants, indicating a device was used/triggered; (5) Actuation Detection via Sound: Microphone mounted to or near the canister listening to sounds from inside the canister, with the canister amplifying sound like a speaker box; (6) Actuation Detection by Chemical Sensor: Chemical/Bio-Marker smell sensor to detect type of drug actuated, and/or to detect propellant released; (7) Actuation Detection by Humidity or Moisture Sensor: Humidity sensor to detect amount of humidity at drug release, therefore confirming actuation; (8) Movement or Handling Sensing and Tracking: Information, interpreting accelerometer data, usage technique; and (9) Location: Geographic or physical location of device, connecting to an application in one embodiment.

Detailed Embodiments of Sensing Inhalation Detection

The current TMAI sits atop the MDI canister and is generally removed from the air inlet of the MDI which is formed by the gap between the pMDI canister outer wall and the inner wall of the pMDI actuator body. In one embodiment, referring to FIGS. 35-39, a plurality of air inlets 330 or channels, shown as two, are formed in the side wall of the EM housing. One or more outlets 332 are also defined in the bottom of the EM. A flow passageway 336 is defined between the inlets 330 and outlet(s) 332. One or more sensors 334 may be located on the bottom of the EM circuit board and located in the flow passageway. In this way, the EM of the eTMAI is configured to determine inhalation sensing. The top mounted dose counter EM is attached to the top of the drug canister 12. An extension, defined as a skirt 320, may be coupled to the EM to extend a plurality of air flow pathway communicating channels 338 into the interior of the MDI boot. The air flow pathway communicating channels 332 are configured to ensure air drawn by the patient during inhalation is moved through the inlet 330 and flow passageway 336 and through the outlet 332 and into the channels 338. As the eTMAI is connected to the canister, the air inlet channels must be allowed to move with respect to the pMDI actuator so that it is not impeded and so effective actuation of the pMDI can take place. As such, the air inlet channel walls can be made of two shot soft silicone rubber material or to fit the MDI shape by matching flexible plastics in a precise way that allows for gaps to be minimized while allowing translation during actuation. Importantly, a relatively leak free and movable seal may be formed to ensure a sufficient and consistent flow of air is drawing through the air inlet channels 338. This ensures that there is sufficient inhalation flow signature for the sensor to register the flow. In one embodiment, flow, pressure, and microphone sensors may be located inside the eTMAI EM. In use, air would be drawn through ports 330 located within the TMAI body, either through existing gaps in the design that would allow sufficient air flow or through dedicated ports 330. Ports would be designed in such a way as to direct a sufficient amount of air flow over the sensor 334.

Referring to FIGS. 35-38, the skirt fitting around the dose counter has a shape that fits in the MDI boot and allows for a sliding movement up and down forming the same air flow pathway communicating channel as above, which allows the air flow to communicate with the eTMAI sensors. The skirt and flow channels may direct air past one or more sensors. For example, the sensor may include a microphone to pick up changes in sound as the flow increases or decreases. Alternatively, a pressure sensor may respond to the vacuum generated during inhalation, which would provide an output that is proximal to flow. In both cases, an algorithm may be used to convert sound or pressure outputs from the sensor into air flow. The flow, sound and/or pressure sensors may be located in the EM or at some point within the flow channel or skirt. In the latter embodiment, this may allow the sensor to be positioned closer to where the source of flow is and thereby increase sensitivity and robustness of the readings. A connector wire or wireless communication may allow the EM to communicate with the sensor.

The container has a first end with a valve stem coupled to the boot, with the electronic module coupled to the opposite second end of the container. The skirt is disposed in the space between an exterior surface of the container and an interior surface of the actuator boot. The skirt extends along a side of the container. The channel 338 extends longitudinally and defines an exit port 340 at a bottom of the skirt Referring to FIG. 37, in one embodiment, the eTMAI includes two units or modules 352, 354, with the module 354 being reusable and rechargeable and the module 352 being consumable or disposable. By bifurcating the modules, production costs may be reduced and also would make it easier for the user to connect to the Smart Phone App since they would not need to customize or program their device every time they buy a new boot. The programing and customization may be done once for the module 354. However, the module 352 may automatically connect to the module 354 upon installation and wake up from deep sleep. The module 354 may be coupled to the exterior of the actuator boot, for example with adhesive, and may include a larger rechargeable battery, while the smaller non reusable unit 352 may include a coin cell battery within the top mounted mechanical counter. The electronic unit 352 attached to the mechanical counter and the canister is not reusable. The two units would communicate together via very low power, with the main unit 354 then transmits a signal further to the smart phone application or other communicating systems.

In order to complete the task of detecting a user button press action, a microcontroller with one or more of a motion, sound, and/or distance sensor may be used. The sensor input data will be processed by the microcontroller, to detect if there was an actuation, e.g., a button push by the user, and then transmitted via wireless communication to a mobile app. The microcontroller does not necessarily require an embedded wireless communication capability to transmit the data to the mobile device. Instead, it may have an external wireless transceiver IC.

Some exemplary selection parameters for the microcontroller selection are listed below where it applies to both microcontrollers with and without embedded wireless communication capability.
Small form factor.
E.g., smaller than VFQFN-20 for microcontroller without BLE transceiver and smaller than VFQFN-48 for microcontroller with internal wireless transceiver.
Able to operate between 1.8 V to 3.6 V supply.
Consists of internal RC oscillator (both fast and slow clocks).
SoCs with embedded wireless transceiver may include external crystals.
Has SPI communication capability.
Needed for microcontrollers without embedded wireless transceiver and need to communicate to an external transceiver such as the nRF24L01+.
SPI (or $I^2C$/TWI) may also be needed if sensors such as IMU is used.
Has ADC block.
Needed for MEMS microphone and IR detector (phototransistor).
Has internal reference voltage for the ADC.
Not required if sensors use SPI (or $I^2C$/TWI).
Low power consumption.
E.g., less than 10 µA in sleep mode.
Has enough RAM and flash for click detection processing (to be determined).
The microcontroller may also include blue tooth. In order to reduce the overall cost of the click detector module, one embodiment includes a separate transceiver for the BLE communication.

The parameters for sensors to be used for clicking sound detection include:
Small form factor.
E.g., smaller than VFQFN-20 and height of less than 1 mm.
Able to operate between 1.8 V to 3.6 V supply.
Uses SPI or $I^2C$ communication if it uses digital communication for data output.
Low power consumption.
E.g., less than 10 µA in low-power mode (averaged for one hour operation).
Another sensor may be an Inertial Measurement Unit 900 (IMU)=gyro, accelerometer, etc. The push button TMAI device generates vibration when the button is pressed down, from both the motion of the button being pressed down as well as from the clicking mechanism for decrementing the mechanical counter. This motion can be captured by an IMU sensor 900 such as an accelerometer.

The vibration generated from an actuation, e.g., a button press, is captured by the IMU sensor 900 which then triggers the interrupt event and sends a wake-up signal to the microcontroller 902. The microcontroller 902 will wake-up from sleep mode and begin recording the IMU sensor data for $T_{IMU}$ seconds. Once the data collection is complete, the recorded data will be processed using DSP algorithms (e.g., FFT or Goertzel algorithm) along with previously recorded profile data of a button push to determine if the button was pushed or not.

The IMU sensor may operate in low-power mode until motion is detected and outputs an event trigger signal for the microcontroller to wake-up (this trigger event occurs if one or more axis readings go above a programmed threshold value). This lowers the overall power consumption for both the IMU and the microcontroller, since the microcontroller does not have to poll continuously to check if motion was detected or not.

One suitable IMU embodiment is a KXTJ3-1057 accelerometer. The IMU sensor includes shake detection capability and consumes relatively low power during both sleep and sensor reading modes (i.e., 0.9 and 10 µA). In one embodiment, the vibrations caused by the button being pushed are due to the clicking sound generated from the spring-like mechanical components within the mechanical dose counter.

In another embodiment, the push button device consists of a mechanical counter that decrements the counter value each time the user pressed down the button. When the counter decrement occurs, a clicking sound is generated which can be captured by a microphone. The clicking sound generated from an actuation is picked up by the microphone and the audio signal is read by the microcontroller ADC. The microcontroller will read the audio data for $T_{ADC}$ seconds. Once the data collection is complete, the recorded audio data will be processed using DSP algorithms (e.g., FFT or Goertzel algorithm) along with previously recorded profile data of a button push to determine if the button was pushed or not. After processing is complete, the microcontroller will go to sleep for $T_{sleep}$ and then repeat the previous steps. In one embodiment, a digital MEMS microphone (with PDM signal output) with internal amplifier may be used.

In another embodiment, small holes are provided underneath the mechanical dose counter where the action of the cap being pressed down can be observed. That is, when the cap is pressed down, the spring-like mechanical component gets closer towards the hole. A proximity sensor, or displacement sensor, would be able to detect the distance of the mechanical component through the hole which in turn detects if the cap and mechanical dose counter has been actuated. The cap press is detected by the microcontroller with the use of a combination of IR detector and emitter. The microcontroller will read the IR detector (phototransistor) data for $T_{ADC\_IR}$ seconds. Once the data collection is complete, the recorded IR intensity (distance) data will be processed to determine if the button was pushed or not. After processing is complete, the microcontroller will go to sleep for $T_{sleep}$ and then repeat the previous steps.

Various microcontrollers operate only in Bluetooth advertising mode or establish a connection between the mobile device and themselves.

Figure 26:
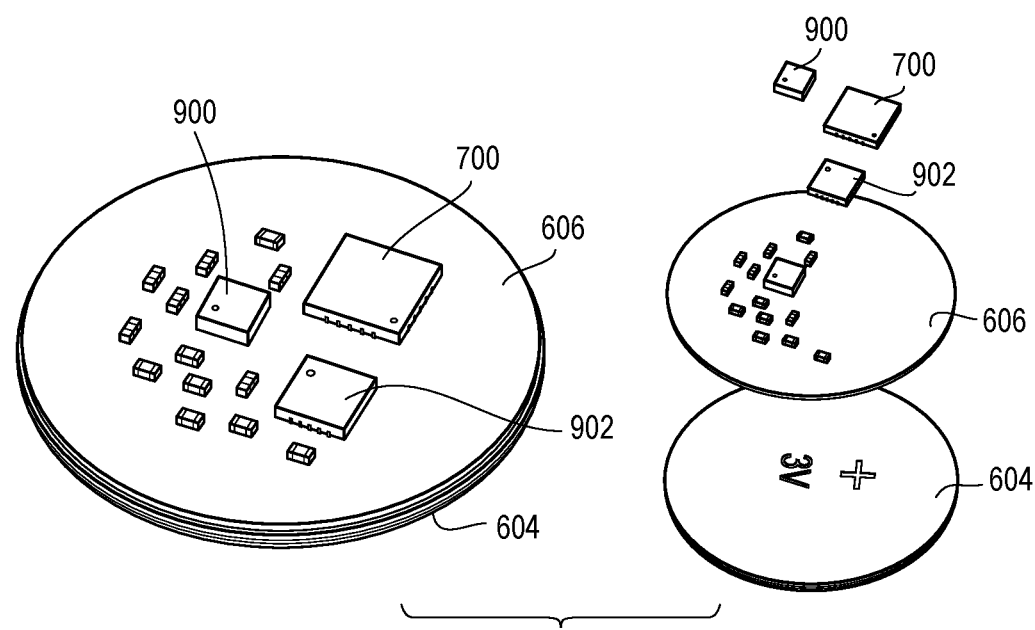
FIG. 26 is an exploded view of one embodiment of an electronic module.
Figure 27:
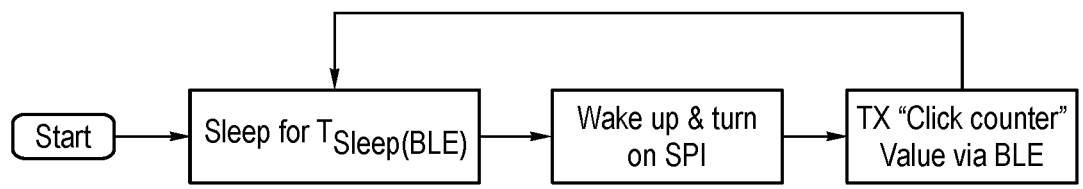
FIG. 27 is a flow chart showing a TX event for BLE advertisement.

As shown in FIG. 26, the EM includes a battery, PCB, and components. The diameter of the entire module is 20 mm and the maximum height between the battery and the largest circuit component (located at the centre with the IC) is 2.55 mm. The height of the module, near the ends of the PCB between battery and the PCB, is 1.6 mm, which means this module can fit into our required volume assuming the indent curvature of the inhaler metal capsule exists.

In order to provide faster and more accurate processing of the sensor data generated within the EM, data may be wirelessly communicated to a smart phone, local computing device and/or remote computing device to interpret and act on the raw sensor data.

In one implementation, the EM includes circuitry for transmitting raw sensor data in real time to a local device, such as a smart phone. The smart phone may display graphics or instructions to the user and implement processing software to interpret and act on the raw data. The smart phone may include software that filters and processes the raw sensor data and outputs the relevant status information contained in the raw sensor data to a display on the smart phone. The smart phone or other local computing device may alternatively use its local resources to contact a remote database or server to retrieve processing instructions or to forward the raw sensor data for remote processing and interpretation, and to receive the processed and interpreted sensor data back from the remote server for display to the user or a caregiver that is with the user of the MDI.

In addition to simply presenting data, statistics or instructions on a display of the smart phone or other local computer in proximity of the MDI configured with an EM, proactive operations relating to the MDI may be actively managed and controlled. For example, if the smart phone or other local computer in proximity to the MDI determines that the sensor data indicates the end of treatment has been reached, the smart phone or other local computing device may communicate directly with the EM to provide a signal, such as an audio or visual signal. In yet other implementations, real-time data gathered in the EM and relayed via to the smart phone to the remote server may trigger the remote server to track down and notify a physician or supervising caregiver regarding a problem with the particular drug delivery session or a pattern that has developed over time based on past sessions for the particular user. Based on data from the one or more sensors in the EM, the remote server may generate alerts to send via text, email or other electronic communication medium to the user's physician or other caregiver.

Figure 30:
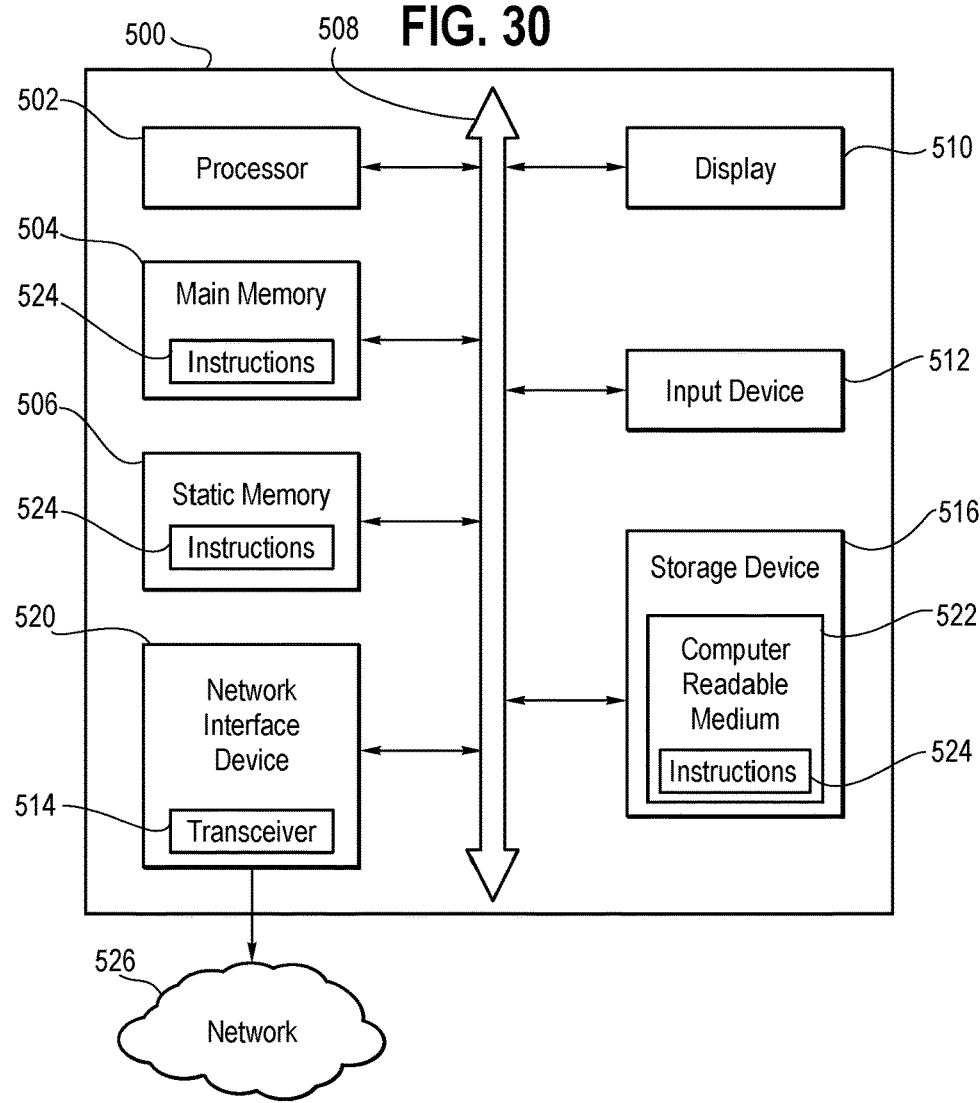
FIG. 30 is a schematic illustrating a computer structure.
Figure 31:
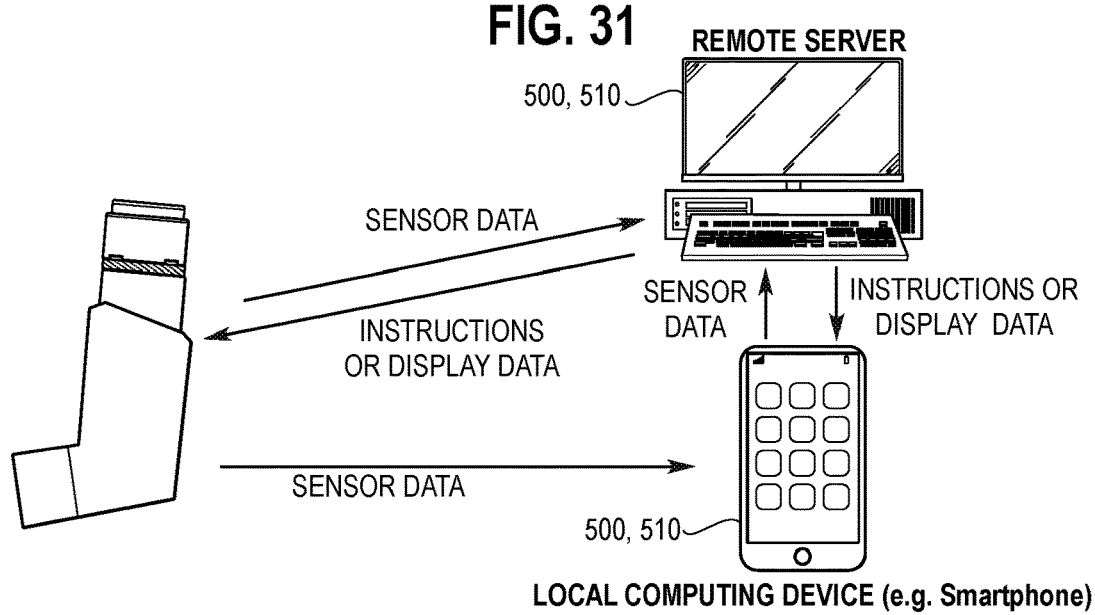
FIG. 31 is a schematic illustration of a communication system.
Figure 32:
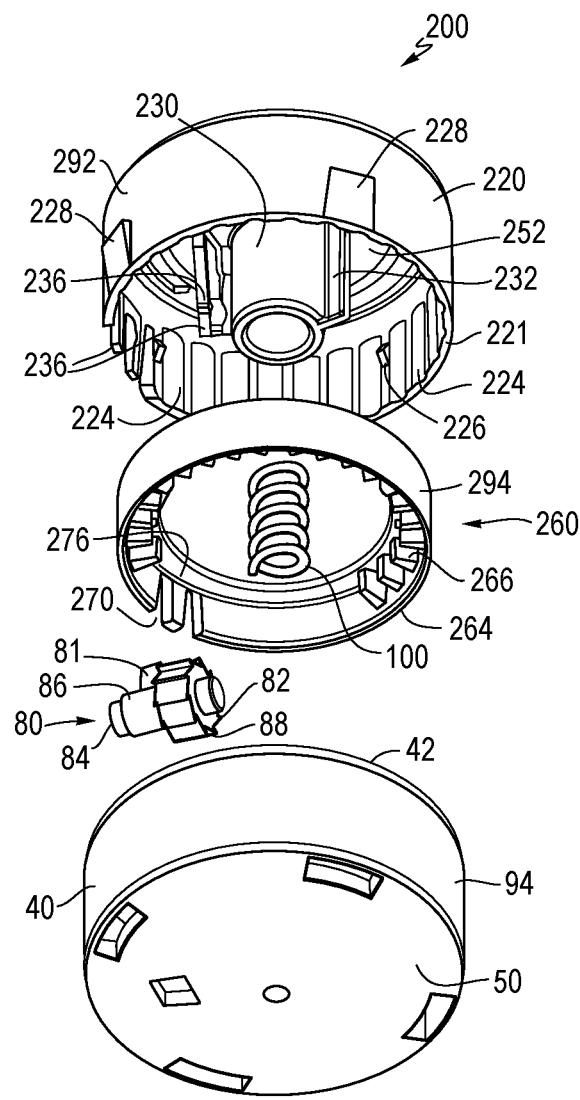
FIG. 32 is an exploded view of a mechanical dose counter.

The electronic circuitry in the EM, the local computing device and/or the remote server discussed above, may include some or all of the capabilities of a computer 500 in communication with a network 526 and/or directly with other computers. As illustrated in FIG. 30, the computer 500 may include a processor 502, a storage device 516, a display or other output device 510, an input device 512, and a network interface device 520, all connected via a bus 508. The computer may communicate with the network. The processor 502 represents a central processing unit of any type of architecture, such as a CISC (Complex Instruction Set Computing), RISC (Reduced Instruction Set Computing), VLIW (Very Long Instruction Word), or a hybrid architecture, although any appropriate processor may be used. The processor 502 executes instructions and includes that portion of the computer 500 that controls the operation of the entire computer. Although not depicted in FIG. 31, the processor 502 typically includes a control unit that organizes data and program storage in memory and transfers data and other information between the various parts of the computer 500. The processor 502 receives input data from the input device 512 and the network 526 reads and stores instructions (for example processor executable code) 524 and data in the main memory 504, such as random access memory (RAM), static memory 506, such as read only memory (ROM), and the storage device 516. The processor 502 may present data to a user via the output device 510.

Although the computer 500 is shown to contain only a single processor 502 and a single bus 508, the disclosed embodiment applies equally to computers that may have multiple processors and to computers that may have multiple busses with some or all performing different functions in different ways.

The storage device 516 represents one or more mechanisms for storing data. For example, the storage device 516 may include a computer readable medium 522 such as read-only memory (ROM), RAM, non-volatile storage media, optical storage media, flash memory devices, and/or other machine-readable media. In other embodiments, any appropriate type of storage device may be used. Although only one storage device 516 is shown, multiple storage devices and multiple types of storage devices may be present. Further, although the computer 500 is drawn to contain the storage device 516, it may be distributed across other computers, for example on a server.

The storage device 516 may include a controller (not shown) and a computer readable medium 522 having instructions 524 capable of being executed on the processor 502 to carry out the functions described above with reference to processing sensor data, displaying the sensor data or instructions based on the sensor data, controlling aspects of the smart nebulizer to alter its operation, or contacting third parties or other remotely located resources to provide update information to, or retrieve data from those remotely located resources. In another embodiment, some or all of the functions are carried out via hardware in lieu of a processor-based system. In one embodiment, the controller is a web browser, but in other embodiments the controller may be a database system, a file system, an electronic mail system, a media manager, an image manager, or may include any other functions capable of accessing data items. The storage device 516 may also contain additional software and data (not shown), which is not necessary to understand the invention.

The output device 510 is that part of the computer 500 that displays output to the user. The output device 510 may be a liquid crystal display (LCD) well-known in the art of computer hardware. In other embodiments, the output device 510 may be replaced with a gas or plasma-based flat-panel display or a traditional cathode-ray tube (CRT) display. In still other embodiments, any appropriate display device may be used. Although only one output device 510 is shown, in other embodiments any number of output devices of different types, or of the same type, may be present. In an embodiment, the output device 510 displays a user interface. The input device 512 may be a keyboard, mouse or other pointing device, trackball, touchpad, touch screen, keypad, microphone, voice recognition device, or any other appropriate mechanism for the user to input data to the computer 500 and manipulate the user interface previously discussed. Although only one input device 512 is shown, in another embodiment any number and type of input devices may be present.

The network interface device 520 provides connectivity from the computer 500 to the network 526 through any suitable communications protocol. The network interface device 520 sends and receives data items from the network 526 via a wireless or wired transceiver 514. The transceiver 514 may be a cellular frequency, radio frequency (RF), infrared (IR) or any of a number of known wireless or wired transmission systems capable of communicating with a network 526 or other smart devices 102 having some or all of the features of the example computer of FIG. 2. The bus 508 may represent one or more busses, e.g., USB, PCI, ISA (Industry Standard Architecture), X-Bus, EISA (Extended Industry Standard Architecture), or any other appropriate bus and/or bridge (also called a bus controller).

The computer 500 may be implemented using any suitable hardware and/or software, such as a personal computer or other electronic computing device. The computer 500 may be a portable computer, laptop, tablet or notebook computers, smart phones, PDAs, pocket computers, appliances, telephones, and mainframe computers are examples of other possible configurations of the computer 500. The network 526 may be any suitable network and may support any appropriate protocol suitable for communication to the computer 500. In an embodiment, the network 526 may support wireless communications. In another embodiment, the network 526 may support hard-wired communications, such as a telephone line or cable. In another embodiment, the network 526 may support the Ethernet IEEE (Institute of Electrical and Electronics Engineers) 802.3x specification. In another embodiment, the network 526 may be the Internet and may support IP (Internet Protocol). In another embodiment, the network 526 may be a LAN or a WAN. In another embodiment, the network 526 may be a hotspot service provider network. In another embodiment, the network 526 may be an intranet. In another embodiment, the network 526 may be a GPRS (General Packet Radio Service) network. In another embodiment, the network 526 may be any appropriate cellular data network or cell-based radio network technology. In another embodiment, the network 526 may be an IEEE 802.11 wireless network. In still another embodiment, the network 526 may be any suitable network or combination of networks. Although one network 526 is shown, in other embodiments any number of networks (of the same or different types) may be present.

It should be understood that the various techniques described herein may be implemented in connection with hardware or software or, where appropriate, with a combination of both. Thus, the methods and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computer, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or use the processes described in connection with the presently disclosed subject matter, e.g., through the use of an API, reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations. Although exemplary embodiments may refer to using aspects of the presently disclosed subject matter in the context of one or more stand-alone computer systems, the subject matter is not so limited, but rather may be implemented in connection with any computing environment, such as a network or distributed computing environment. Still further, aspects of the presently disclosed subject matter may be implemented in or across a plurality of processing chips or devices, and storage may similarly be spread across a plurality of devices. Such devices might include personal computers, network servers, and handheld devices, for example.

Figure 43:
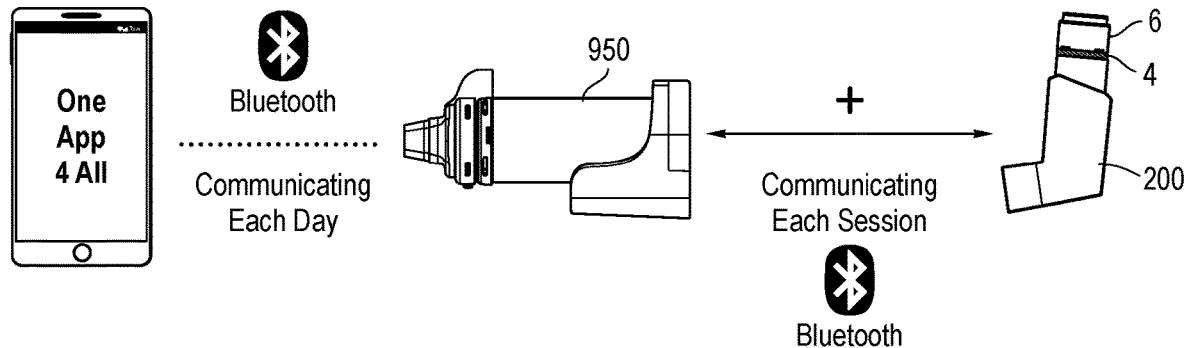
FIG. 43 is a side schematic view showing the communication between a pressurized metered dose inhaler, valved holding chamber and local computing device.
Figure 44:
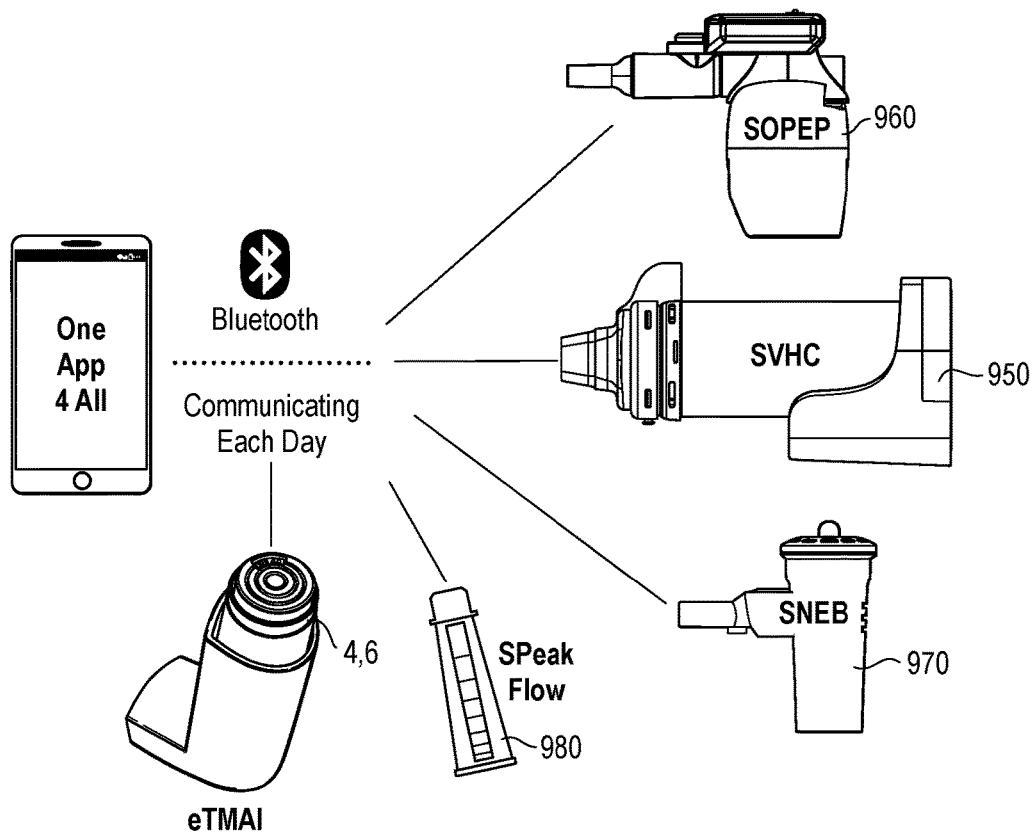
FIG. 44 is a schematic view showing communication between various smart devices.

Referring to FIGS. 43-45, the eTMAI 4, 6 is designed such that it may communicate with other nearby devices if required, and may include one or more connection protocols, including: (1) Proximity (0-10 m): NFC, RFID; (2) Wireless Personal Area Network (10-100 m): BLE, ZigBee, ISA100; (3) Wireless Local Area Network (100-1000 m): 802.11 IEEE; (4) Wireless Neighborhood Area Network (~5-10 km): Wi-SUN; and/or (5) Wireless Wide Area Network (up to 100 km): Cellular (LTE CAT M1, 4G, 5G, LPWAN, SigFox, LoRa).

In one embodiment, shown in FIG. 43, a smart valved holding chamber 50 (SVHC) may communicate with the eTMAI 4, 6 To best confirm that the drug released by the eTMAI was inhaled, the SVHC 950 may could sense inhalation detection and inhalation completion if used in line with the eTMAI, this adherence method ensures that the medication was inhaled/delivered, and the patient took a breath in. The adherence data captured by the eTMAI and the SVHC are communicated to the SVHC Smart Phone Application where they are analyzed and displayed on the screen. Inhalation confirmation is the combination of inhalation detection and inhalation completion. The VHC/SVHC helps properly deliver the correct amount of drug to the lungs and not to the back of the throat. The sVHC may also recognize Actuation Detection, Inhalation Detection, Inhalation Completion, and provide Event Time Stamp. The combination thereby provides greater value (assurance and credibility) to the user and the adherence tracking record. At the same time, the eTMAI can recognize the drug used and the number of doses left in the canister. Referring to FIG. 44, the eTMAI is connected to the Smartphone Application and the other related medical devices, which may include a smart oscillating positive expiratory pressure device 960, a smart nebulizer device 970, a smart valved holding chamber 950, and/or a smart peak flow device 980. The eTMAI is able to connect to a range of other smart devices in the close vicinity as such. In an exemplary connected environment, a virtual assistant may be connected to provide reminders to the user to take a certain medication, or a Philips Hue programed light may provide a visual output, e.g., a certain color at a certain time, as a reminder of what MDI drug to take. Alternatively, a smart watch may provide reminders regarding the time and type of medication to take.

Alternative Feedback Embodiments

In another embodiment, a haptic feedback module may be located inside the eTMAI, producing a vibration notifying the user by buzzing at different frequencies, which may be programmed by the user in an application settings.

In other embodiments, speakers may provide auditory or sound feedback, including for example musical tones, and/or a speaking voice notifying user with activity events such as: (a) One buzzing or beep, good technique, accompanied by a green LED, or vice versa; (b) Two buzzing or beeps, poor technique, accompanied by a red LED, or vice versa; (c) Buzzing with a tone or melody (programmable via app), reminding user to take their medication at pre-set times.

In other embodiments, a scent emitting system may provide olfactory or smell feedback, including a device to emit a scent A if drug A is used and a scent B if drug B is used. The scent emitter may be a scratch sniff label installed by the manufacture of the medicament. The scent emitting system may be especially beneficial to hearing or vision impaired individuals when identifying the medicament being dispensed by the MDI.

In another embodiment, the device may be configured with a brail indicator 804, for example including On/OFF protruding features, or indicate in brail a character representing Drug A, and another character representing Drug B canisters by touch.

In another embodiment, the system may be configured with a locater device, activated for example by pressing an icon on an application to locate the nearby inhaler, or by incorporating hardware in the system that is reactive to auditory inputs, such as whistling or clapping, with the device emitting, e.g. with a microphone, an auditory output or signal, for example a whistle or return sound.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

The invention claimed is:

1. An indicating device comprising:
a mechanical dose counter comprising a cap moveable relative to a base along a longitudinal axis between first and second positions when a predetermined force is applied to the cap, wherein the mechanical dose counter is adapted to register a movement of the cap relative to the base and a corresponding actuation of a medicament container in response to the application of the predetermined force, and wherein the base comprises a bottom configured to be coupled to the medicament container; and
an electronic module coupled directly to the bottom of the base of the mechanical dose counter such that the electronic module is adapted to be positioned above the medicament container, wherein the electronic module comprises a displacement sensor responsive to the movement of the cap relative to the base between the first and second positions, and wherein the electronic module is adapted to record the relative movement of the cap and base between the first and second positions in response to an input from the displacement sensor.

2. The indicating device of claim 1 wherein at least one of the base and the electronic module are adapted to be coupled to the container.

3. The indicating device of claim 1 wherein the electronic module has a cross-sectional area orthogonal to the longitudinal axis less than or equal to a cross-sectional area of the mechanical dose counter orthogonal to the longitudinal axis.

4. The indicating device of claim 1 wherein the electronic module comprises a force sensor.

5. The indicating device of claim 1 wherein the electronic module comprises an inertial measurement unit sensor.

6. The indicating device of claim 5 wherein the inertial measurement unit sensor comprises an accelerometer.

7. The indicating device of claim 1 wherein the electronic module comprises a microphone.

8. The indicating device of claim 7 wherein the microphone is adapted to pick up an actuation sound of the mechanical dose counter in response to the movement of the component between the first and second positions.

9. The indicating device of claim 1 wherein the displacement sensor comprises an infrared displacement sensor.

10. A medication delivery device comprising the medicament container and the indicating device of claim 1, wherein the medicament container is coupled to the electronic module, wherein the electronic module is disposed between the cap and the medicament container.

11. The medication delivery device of claim 10 further comprising a wrap surrounding at least peripheral portions of the container and least one of the base and/or the electronic module, wherein the wrap couples the container to the at least one of the base and/or electronic module.

12. The medication delivery device of claim 10 wherein the electronic module is adapted to record when the doses have been dispensed from the container.

13. An indicating device comprising:
a mechanical dose counter comprising a cap moveable relative to a base along a longitudinal axis between first and second positions when a predetermined force is applied to the cap, wherein the mechanical dose counter is adapted to register a movement of the cap relative to the base and a corresponding actuation of a medicament container in response to the application of the predetermined force, and wherein the base comprises a bottom configured to be coupled to the medicament container;
an electronic module coupled directly to the bottom of the base of the mechanical dose counter such that the electronic module is adapted to be positioned above the medicament container, and wherein the electronic module is adapted to record the relative movement of the cap and base; and a wrap surrounding at least peripheral portions of the base and electronic module, wherein the wrap couples the base to the electronic module.

14. The indicating device of claim 13 wherein the electronic module comprises an LED.

15. The indicating device of claim 14 wherein the wrap is translucent and covers the LED.

16. A method of assembling a medicament dispensing device comprising:

coupling a base of a mechanical dose counter adapted to count a number of doses that have been dispensed from or remain in a container to an electronic module adapted to record when the doses have been dispensed from the container, wherein the mechanical dose counter comprises a cap moveable relative to the base along a longitudinal axis between first and second positions when a predetermined force is applied to the cap, wherein the electronic module comprises a displacement sensor responsive to the movement of the cap relative to the base between the first and second positions, and wherein the electronic module is adapted to record the relative movement of the cap and base between the first and second positions in response to an input from the displacement sensor;

coupling one of the base or the electronic module directly to the container, wherein the electronic module is positioned between the cap and the container; and coupling the container to an actuator housing.

17. The method of claim 16 wherein the displacement sensor comprises an infrared displacement sensor.

18. A method of assembling a medicament dispensing device comprising:

coupling a base of a mechanical dose counter adapted to count a number of doses that have been dispensed from or remain in a container to an electronic module adapted to record when the doses have been dispensed from the container, wherein the mechanical dose counter comprises a cap moveable relative to the base along a longitudinal axis between first and second positions when a predetermined force is applied to the cap, and wherein the electronic module is adapted to record the relative movement of the cap and base between the first and second positions;

coupling one of the base or the electronic module directly to the container, wherein the electronic module is positioned between the cap and the container, wherein the coupling of the base or the electronic module directly to the container comprises wrapping a wrap around at least peripheral portions of the container and at least one of the base and/or the electronic module, and engaging the peripheral portions of the container and the at least one of the base and/or electronic module with the wrap; and coupling the container to an actuator housing.

19. The method of claim 18 wherein the electronic module has a cross-sectional area orthogonal to the longitudinal axis less than or equal to a cross-sectional area of the mechanical dose counter orthogonal to the longitudinal axis.

* * * * *